US009108915B2

(12) United States Patent
Araya et al.

(10) Patent No.: US 9,108,915 B2

(45) Date of Patent: Aug. 18, 2015

(54) METHOD FOR PRODUCING 3,4-DISUBSTITUTED PYRROLIDINE DERIVATIVE

(75) Inventors: Ichiro Araya, Tochigi (JP); Koichi Kiyota, Tochigi (JP); Muneki Nagao, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/880,207

(22) PCT Filed: Oct. 24, 2011

(86) PCT No.: PCT/JP2011/074463

§ 371 (c)(1), (2), (4) Date: Apr. 18, 2013

(87) PCT Pub. No.: WO2012/057093

PCT Pub. Date: May 3, 2012

(65) Prior Publication Data

US 2013/0217893 A1 Aug. 22, 2013

(30) Foreign Application Priority Data

Oct. 25, 2010 (JP) ................................ 2010-238077

(51) Int. Cl.

*C07D 207/16* (2006.01)
*C07D 207/24* (2006.01)
*C07B 53/00* (2006.01)
*C07C 269/06* (2006.01)
*C07C 227/18* (2006.01)
*C07D 207/277* (2006.01)

(52) U.S. Cl.

CPC .............. *C07D 207/24* (2013.01); *C07B 53/00* (2013.01); *C07C 227/18* (2013.01); *C07C 269/06* (2013.01); *C07D 207/16* (2013.01); *C07D 207/277* (2013.01); *C07C 2101/02* (2013.01)

(58) Field of Classification Search

CPC .................................................... C07D 207/16

USPC ......................................................... 548/537

See application file for complete search history.

(56) References Cited

U.S. PATENT DOCUMENTS 7,667,049 B2 * 2/2010 Gotoh et al. .................. 548/566
2005/0182052 A1 8/2005 Asahina et al.
2006/0281779 A1 12/2006 Asahina et al.
2009/0023935 A1 * 1/2009 Gotoh et al. .................. 548/536
2009/0176824 A1 7/2009 Asahina et al.
2010/0056805 A1 3/2010 Gotoh et al.

FOREIGN PATENT DOCUMENTS

JP 2005-239617 9/2005
WO 03/078439 9/2003
WO 2005/026147 3/2005
WO 2007/102567 9/2007

OTHER PUBLICATIONS

Noyori et al. (Angewandte Chemie International Edition, vol. 40, Issue 1, pp. 40-73, Jan. 5, 2001).*
Kitamura et al. (J. Am. Chem. Soc., 1988, v. 110, p. 629-631).*
Trost (Comprehensive Organic Synthesis, vol. 2, Part 2. (1991)). Chapter 3.6 provided.*
March's Advanced Organic Chemistry, 5th ed., (2001). Chapters 10 and 16 provided.*
Carey et al. ("Planning and Execution of Multistep Syntheses," Reactions and Synthesis, Part B, (2001), p. 821-922).*
International Search Report issued Nov. 22, 2011 in International (PCT) Application No. PCT/JP2011/074463.
J. Limanto et al., "Dynamic Kinetic Resolution: Asymmetric Transfer Hydrogenation of α-Alkyl-Substituted β-Ketoamides", Organic Letters, vol. 12, No. 3, pp. 512-515, 2010.
Supplementary European Search Report issued Jan. 8, 2014 in European Application No. 11 83 6226.
Sibi et al., "Chemoselective Dieckmann-Like Condensations Using N-Methoxy-N-Methylamides", Tetrahedron Letters, vol. 36, No. 35, 1995, pp. 6209-6212.
R. Noyori, et al., "Stereoselective Hydrogenation via Dynamic Kinetic Resolution", J. Am. Chem. Soc., 1989, vol. 111, pp. 9134-9135.

* cited by examiner

*Primary Examiner* — Robert Havlin

(74) *Attorney, Agent, or Firm* — Wenderoth, Lind & Ponack, L.L.P.

(57) ABSTRACT

The present invention provides an inexpensive and industrially advantageous method for producing an optically active form of an anti-(3S,4R)-3-alkylcarbamoyl-4-hydroxypyrrolidine derivative or it's enantiomer, which is a key intermediate for producing a high-quality optically active form of (3R,4S)-3-alkylaminomethyl-4-fluoropyrrolidine or it's enantiomer useful as an intermediate for producing pharmaceuticals.

The present invention relates to a method for producing an optically active anti-(3S,4R)-4-hydroxypyrrolidine-3-carboxamide derivative, or it's enantiomer by carrying out asymmetric hydrogenation using an optically active catalyst of a 4-oxopyrrolidine-3-carboxamide derivative represented by the general formula (I).

[Chem. 1]

(I)

O, O, NH, $R_1$, N, $PG_1$

[in the formula (I), $PG^1$ represents a protective group for an amino group, and $R^1$ represents hydrogen, a C1 to C6 alkyl group which may be substituted, or a C3 to C8 cycloalkyl group which may be substituted].

18 Claims, No Drawings

METHOD FOR PRODUCING 3,4-DISUBSTITUTED PYRROLIDINE DERIVATIVE

TECHNICAL FIELD

The present invention relates to a novel method for producing a 3,4-disubstituted pyrrolidine derivative, which is an intermediate for production of antibacterial agents which are effective also to resistant bacteria.

PRIOR ART

Patent Documents 1 and 2 disclose a 10-(3-cyclopropylaminomethyl-4-substituted 1-pyrrolidinyl)pyridobenzoxazinecarboxylic acid derivative and a 7-(3-cyclopropylaminomethyl-4-substituted 1-pyrrolidinyl)quinolonecarboxylic acid derivative as antibacterial agents which show excellent antibacterial activities on resistant bacteria and are highly safe.

However, the compounds described in Patent Documents 1 and 2 have a (3R,4S)-3-alkylaminomethyl-4-fluoropyrrolidinyl group at the 10-position or the 7-position, but for the synthesis of its raw material, that is, (3R,4S)-3-alkylaminomethyl-4-fluoropyrrolidine, there have been problems such as multi-step process (Patent Documents 1 and 2) and the difficulty in purification (Patent Document 3).

Therefore, in Patent Document 4, an improved method for producing an α-substituted β-ketoester derivative using an asymmetric hydrogenation reaction has been disclosed. That is, it is disclosed that an optically active form of an anti-(3S,4R)-3-alkoxycarbonyl-4-hydroxypyrrolidine derivative or it's enantiomer can be obtained with high stereoselectivity by carrying out asymmetric hydrogenation using an optically active catalyst of a racemic 3-alkoxycarbonyl-4-oxopyrrolidine derivative.

In addition, it is disclosed that an optically active form of an anti-(3S,4R)-3-alkylcarbamoyl-4-hydroxypyrrolidine derivative is obtained by converting an ester group moiety of the obtained optically active form of the anti-(3S,4R)-3-alkoxycarbonyl-4-hydroxypyrrolidine derivative into an alkylamide group.

The compound has superior crystallinity, and the enantiomer [(3R,4S)-form] and it's diastereomers of the desired product, which are produced in small amounts from the asymmetric hydrogenation step, can be removed by recrystallization or the like. Thereafter, an optically active form of (3R,4S)-3-alkylaminomethyl-4-fluoropyrrolidine may be derived through the step such as fluorination of a hydroxyl group (Patent Document 4).

Furthermore, similarly, in the case of using an optically active form of an anti-(3R,4S)-3-alkoxycarbonyl-4-hydroxypyrrolidine derivative, an optically active form of a (3S,4R)-3-alkylaminomethyl-4-fluoropyrrolidine may be derived (Patent Document 4).

On the other hand, there are few examples of catalytic asymmetric hydrogenation reactions using an α-substituted β-ketoamide derivative. In Non-Patent Document 1, examples of the catalytic asymmetric hydrogenation using an α-alkyl-β-ketoamide are described.

PRIOR ART DOCUMENT

Patent Documents

[Patent Document 1] International Publication WO 2003/078439

[Patent Document 2] International Publication WO 2005/026147

[Patent Document 3] Japanese Patent Publication JP-A-2005-239617

[Patent Document 4] International Publication WO 2007/102567

Non-Patent Document

[Non-Patent Document 1] Organic Letters, 2010, 12(3), 512-515

SUMMARY OF INVENTION

Problems to be Solved by the Invention

The production method described in International Publication WO 2007/102567 (Patent Document 4) is significantly useful in that it has a small number of steps involved and permits easy purification, but it provides problems that high-pressure conditions are required when carrying out an asymmetric hydrogenation reaction and a large amount of catalysts are used. In addition, the main product obtained as a desired product in Organic Letters, 2010, 12(3), 512-515 (Non-Patent Document 1) is a syn-β-hydroxyamide form and does not provide the anti-form as a main product.

Therefore, the present invention provides an inexpensive and industrially advantageous method for producing an optically active form of an anti-(3S,4R)-3-alkylcarbamoyl-4-hydroxypyrrolidine derivative or it's enantiomer, which is a key intermediate for producing a high-quality optically active form of (3R,4S)-3-alkylaminomethyl-4-fluoropyrrolidine or it's enantiomer useful as an intermediate for producing pharmaceuticals.

Means for Solving the Problems

The present inventors have made extensive studies in order to solve the above-described problems, and as a result, they have found that an anti-(3S,4R)-4-hydroxypyrrolidine-3-carboxamide derivative or it's enantiomer is obtained with high optical purity by carrying out catalytic asymmetric hydrogenation using a racemic 4-oxopyrrolidine-3-carboxamide derivative, thereby completing the present invention (Step A).

In addition, they have found that a 4-oxopyrrolidine-3-carboxamide derivative which is a reaction starting material for the asymmetric hydrogenation can be synthesized efficiently by a step of using a 3-[(alkoxycarbonylmethyl)amino] propionic acid ester derivative as a raw material and selectively converting one of ester groups into carboxylic acid (Step D), a step of subjecting the obtained monocarboxylic acid derivative to amidation (Step C), and a step of carrying out Dieckmann cyclization (Step B), thereby completing the present invention.

That is, the present invention includes the following inventions.

A method for producing an optically active anti-4-hydroxypyrrolidine-3-carboxamide derivative represented by the general formula (II) or it's enantiomer by carrying out an asymmetric hydrogenation using an optically active catalyst of a 4-oxopyrrolidine-3-carboxamide derivative represented by the general formula (I) (Step A).

[Chem. 1]

(I)

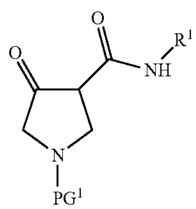

[In the formula (I), $PG^1$ represents a protecting group for an amino group, and $R^1$ represents hydrogen, a C1 to C6 alkyl group which may be substituted, or a C3 to C8 cycloalkyl group which may be substituted.]

[Chem. 2]

(II)

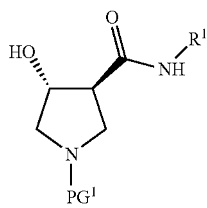

[In the formula (II), $PG^1$ and $R^1$ have the same meanings as described above.]

A method for producing an optically active anti-4-hydroxypyrrolidine-3-carboxamide derivative represented by the general formula (II) or it's enantiomer, comprising Steps B and A below:

(Step B) a step of treating a compound represented by the general formula (III) with at least one kind of base selected from an alkali metal carbonate, an alkali metal amide, an alkali metal hydride, and an alkali metal alkoxide to obtain a 4-oxopyrrolidine-3-carboxamide derivative represented by the general formula (I); and (Step A) a step of subjecting the compound represented by the general formula (I) obtained in Step B to asymmetric hydrogenation using an optically active catalyst to obtain a compound represented by the general formula (II)) or it's enantiomer.

[Chem. 3]

(III)

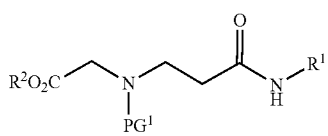

[In the formula (III), $PG^1$ represents a protecting group for an amino group, $R^1$ represents hydrogen, a C1 to C6 alkyl group which may be substituted, or a C3 to C8 cycloalkyl group which may be substituted, and $R^2$ represents a C1 to C6 alkyl group.]

[Chem. 4]

(I)

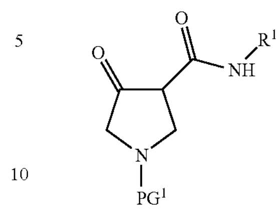

[In the formula (I), $PG^1$ and $R^1$ have the same meanings as described above.]

[Chem. 5]

(II)

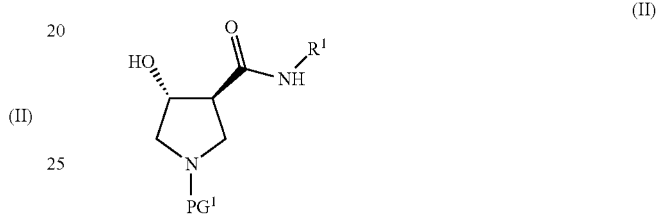

[In the formula (II), $PG^1$ and $R^1$ have the same meanings as described above.]

A method for producing an optically active anti-4-hydroxypyrrolidine-3-carboxamide derivative represented by the general formula (II) or it's enantiomer, comprising Steps D to A below:

(Step D) a step of treating a compound represented by the general formula (IV) with an acid to obtain a compound represented by the general formula (V);

(Step C) a step of condensing the compound represented by the general formula (V) obtained in Step D with an amine represented by the general formula (VI) to obtain a compound represented by the general formula (III);

(Step B) a step of treating the compound represented by the general formula (III) obtained in Step C with at least one kind of base selected from an alkali metal carbonate, an alkali metal amide, an alkali metal hydride, and an alkali metal alkoxide to obtain a 4-oxopyrrolidine-3-carboxamide derivative represented by the general formula (I);

(Step A) a step of subjecting the compound represented by the general formula (I) obtained in Step B to asymmetric hydrogenation using an optically active catalyst having a chiral ligand to obtain a compound represented by the general formula (II) or it's enantiomer.

[Chem. 6]

(IV)

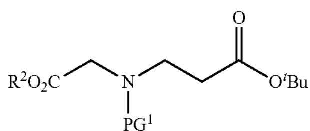

[In the formula (IV), $PG^1$ represents a protecting group for an amino group and $R^2$ represents a C1 to C6 alkyl group.]

[Chem. 7]

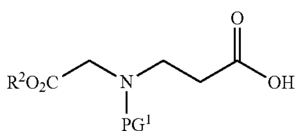

[In the formula (V), $PG^1$ and $R^2$ have the same meanings as described above.]

[Chem. 8]

$R^1$—$NH_2$ (VI)

[In the formula (VI), $R^1$ represents hydrogen, a C1 to C6 alkyl group which may be substituted, or a C3 to C8 cycloalkyl group which may be substituted.]

[Chem. 9]

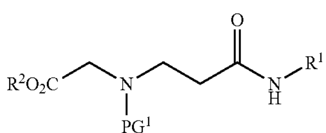

[In the formula (III), $PG^1$, $R^1$, and $R^2$ have the same meanings as described above.]

[Chem. 10]

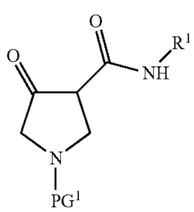

[In the formula (I), $PG^1$ and $R^1$ have the same meanings as described above.]

[Chem. 11]

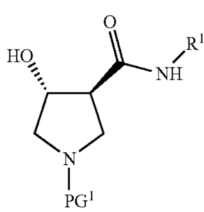

[In the formula (II), $PG^1$ and $R^1$ have the same meanings as described above.]

The production method described in any one of [1] to [3] above, wherein the optically active catalyst in Step A is an optically active ruthenium catalyst having a chiral ligand.

The production method described in any one of [1] to [4] above, wherein in Step A, the chiral ligand in the optically active catalyst is an optically active 2,2'-bis(diphenylphosphino)-1,1'-binaphthyl(BINAP) or it's analogue, 5,5'-bis(diphenylphosphino)-4,4'-bi-1,3-benzodioxole (SEGPHOS) or it's analogue, or (2,2'-bisdiphenylphosphino)-6,6'-dimethoxy-1,1'-biphenyl (MeO-BIPHEP) or it's analogue.

The production method described in any one of [1] to [5] above, wherein in Step A, the chiral ligand in the optically active catalyst is 2,2'-bis(diphenylphosphino)-1,1'-binaphthyl(BINAP) or 5,5'-bis(diphenylphosphino)-4,4'-bi-1,3-benzodioxole (SEGPHOS).

The production method described in any one of [1] to [6] above, wherein the protecting group for the amino group represented by $PG^1$ is an aralkoxycarbonyl group or an alkoxycarbonyl group.

The production method described in any one of [1] to [7] above, wherein the protecting group for the amino group represented by $PG^1$ is an aralkoxycarbonyl group.

The production method described in any one of [1] to [8] above, wherein the protecting group for the amino group represented by $PG^1$ is a benzyloxycarbonyl group.

The production method described in any one of [1] to [9] above, wherein $R^1$ is a cyclopropyl group.

The production method described in any one of [1] to [10] above, wherein the reaction in Step A is carried out under the conditions of a hydrogen pressure of from ordinary pressure to less than 1 MPa.

The production method described in any one of [1] to [11] above, wherein the optically active catalyst in Step A is used in an amount of from 0.01 to 2 mol %, with respect to the general formula (I).

The production method described in any one of [1] to [12] above, wherein the optically active catalyst in Step A is used in an amount of from 0.01 to 1 mol %, with respect to the general formula (I).

A method for producing a compound represented by the general formula (I) for the asymmetric hydrogenation using an optically active catalyst, comprising (Step B) a step of treating the compound represented by the general formula (III) with a base selected from an alkali metal carbonate, an alkali metal amide, an alkali metal hydride, and an alkali metal alkoxide to obtain a 4-oxopyrrolidine-3-carboxamide derivative represented by the general formula (I).

[Chem. 12]

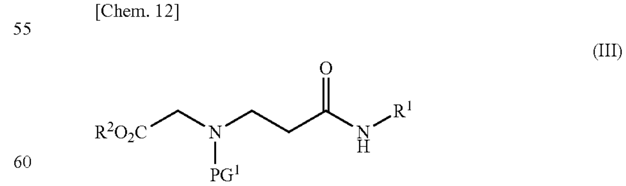

[In the formula (III), $PG^1$ represents a protective group for an amino group, $R^1$ represents hydrogen, a C1 to C6 alkyl group which may be substituted, or a C3 to C8 cycloalkyl group which may be substituted, and $R^2$ represents a C1 to C6 alkyl group.]

[Chem. 13]

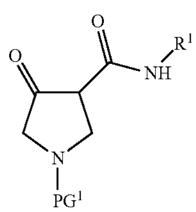

[In the formula (I), $PG^1$ and $R^1$ have the same meanings as described above.]

The production method described in any one of [2] to [14] above, wherein the base in Step B is an alkali metal alkoxide.

The production method described in any one of [2] to [15] above, wherein the base in Step B is potassium tert-pentoxide.

The production method described in any one of [2] to [16] above, wherein the base in Step B is used in the amount of from 1 to 1.5 equivalents, with respect to the compound represented by the general formula (III).

The production method described in any one of [1] to [17] above, wherein the protecting group for the amino group represented by $PG^1$ is an aralkoxycarbonyl group and $R^1$ is a cyclopropyl group.

A method for producing a compound represented by the general formula (V), comprising (Step D) treating a compound represented by the general formula (IV) with an acid.

[Chem. 14]

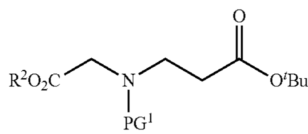

[In the formula (IV), $PG^1$ represents a protective group for an amino group and $R^2$ represents a C1 to C6 alkyl group.]

[Chem. 15]

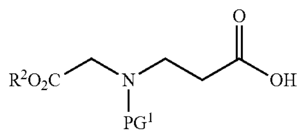

[In the formula (V), $PG^1$ and $R^2$ have the same meanings as described above.]

The production method described in any one of [3] to [13] above and [19] above, wherein the acid in Step D is trifluoroacetic acid or formic acid.

The production method described in any one of [3] to [13], [19], and [20] above, wherein the acid in Step D is formic acid.

The production method described in any one of [2] to [21] above, wherein the protecting group for the amino group represented by $PG^1$ is an aralkoxycarbonyl group and $R^2$ is a C1 to C4 lower alkyl group.

Effects of the Invention

According to the present invention, a racemic 4-oxopyrrolidine-3-carboxamide derivative represented by the general formula (I) can be obtained in high yield.

Furthermore, according to the present invention, an optically active form of an anti-(3S,4R)-4-hydroxypyrrolidine-3-carboxamide derivative, or it's enantiomer can be obtained with high optical purity by carrying out asymmetric hydrogenation using an optically active catalyst of a racemic 4-oxopyrrolidine-3-carboxamide derivative.

An optically active form of an anti-(3S,4R)-4-hydroxypyrrolidine-3-carboxamide derivative, or it's enantiomer obtained by the method of the present invention can be converted to an optically active form of (3R,4S)-3-alkylaminomethyl-4-fluoropyrrolidine or it's enantiomer useful as an intermediate for producing pharmaceuticals by a known method (International Publication WO 2007/102567).

Therefore, according to the present invention, an industrial production method for an optically active form of (3R,4S)-3-alkylaminomethyl-4-fluoropyrrolidine or it's enantiomer is provided.

EMBODIMENTS FOR CARRYING OUT THE INVENTION

Hereinbelow, the present invention will be described in detail.

The production method of the present invention will be described in Scheme 1.

Scheme 1

[Chem. 16]

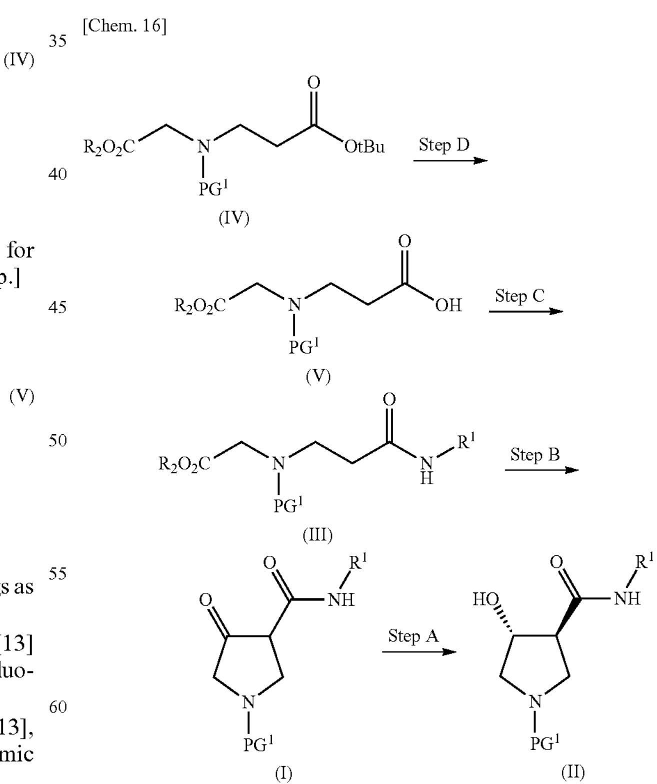

In the formulae (I) to (V), $PG^1$ represents a protecting group for an amino group. In the formulae (I) to (III), $R^1$ represents hydrogen, a C1 to C6 alkyl group which may be substituted, or a C3 to C8 cycloalkyl group which may be substituted. In the formulae (III) to (V), $R^2$ represent a C1 to C6 alkyl group, and preferably a C1 to C4 lower alkyl group.

As described in the present specification, the "protecting group for an amino group" is not particularly limited as long as the protecting group is commonly known as a protecting group for an amino group, and may include, for example, an aralkyl group such as benzyl group or a p-methoxybenzyl group, an alkoxycarbonyl group such as a methoxycarbonyl group, an ethoxycarbonyl group, a propyloxycarbonyl group, an isopropyloxycarbonyl group, a butyloxycarbonyl group, an isobutyloxycarbonyl group or a tert-butyloxycarbonyl group, an aralkoxycarbonyl group such as a benzyloxycarbonyl group, a p-methoxybenzyloxycarbonyl group or a p-nitrobenzyloxycarbonyl group, a 1-(alkoxy)alkyl group such as a methoxymethyl group, a methoxyethoxymethyl group, a 1-(ethoxy)ethyl group or a methoxyisopropyl group, an acyl group such as an acetyl group, a trifluoroacetyl group, a propionyl group, a butyryl group, a pivaloyl group, a benzoyl group or a methylbenzoyl group, or the like.

Among these, an aralkoxycarbonyl group or an alkoxycarbonyl group is preferred, an aralkoxycarbonyl group is more preferred, and a benzyloxycarbonyl group is even more preferred.

As described in the present specification, the "C1 to C6 alkyl group which may be substituted" means a C1 to C6 alkyl group which may have one to five substituents selected from the group consisting of a halogen atom, a hydroxyl group, a cyano group, a C1 to C6 alkoxy group, an aryloxy group which may be substituted, a C1 to C6 alkylcarbonyl group, a C1 to C6 alkoxycarbonyl group, a C1 to C6 alkylthio group, an amino group, a mono- or di-substituted C1 to C6 alkylamino group, a C4 to C9 cyclic amino group which may include one to three hetero atoms, a formylamino group, a C1 to C6 alkylcarbonylamino group, a C1 to C6 alkoxycarbonylamino group, a C1 to C6 alkylsulfonylamino group and an arylsulfonylamino group which may be substituted.

The "C1 to C6 alkyl group" means a straight chain or branched alkyl group. Examples of the C1 to C6 alkyl group may include a methyl group, an ethyl group, a propyl group, a 1-methylethyl group, a 1-methylpropyl group, a 2-methylpropan-1-yl group, a tert-butyl group, a 1-ethylpropyl group, a 2-ethylpropyl group, a butyl group, a hexyl group, or the like. Among these, an ethyl group or a tert-butyl group is preferred.

As described in the present specification, the "C3 to C8 cycloalkyl group which may be substituted" means a C3 to C8 cycloalkyl group which may have one to five substituents selected from the group consisting of a halogen atom, a hydroxyl group, a cyano group, a C1 to C6 alkoxy group, an aryloxy group which may be substituted, a C1 to C6 alkylcarbonyl group, a C1 to C6 alkoxycarbonyl group, a C1 to C6 alkylthio group, an amino group, a mono- or di-substituted C1 to C6 alkylamino group, a C4 to C9 cyclic amino group which may include one to three hetero atoms, a formylamino group, a C1 to C6 alkylcarbonylamino group, a C1 to C6 alkoxycarbonylamino group, a C1 to C6 alkylsulfonylamino group and an arylsulfonylamino group which may be substituted.

The "C3 to C8 cycloalkyl group" means an alkyl group having a cycloalkyl ring. Examples of the C3 to C8 cycloalkyl group may include, for example, a cyclopropyl group, a cyclopropylmethyl group, a cyclobutyl group, a cyclopentyl group, a cyclohexyl group, a cycloheptyl group, a cyclooctyl group, or the like, and a cyclopropyl group is preferred.

Examples of the "C1 to C6 alkoxy group" may include, for example, a methoxy group, an ethoxy group, a butoxy group, a hexyloxy group, or the like.

The "aryloxy group which may be substituted" means an aryloxy group which may have one to five substituents selected from a group consisting of a halogen atom, a hydroxyl group, a cyano group, a nitro group, a C1 to C6 alkyl group, a C1 to C6 alkoxy group and a C1 to C6 alkylthio group.

Examples of the "aryloxy group" may include, for example, a phenoxy group, a naphthyloxy group, or the like.

Examples of the "C1 to C6 alkylcarbonyl group" may include, for example, an acetyl group, a propionyl group, a butyryl group, an isobutyryl group, a valeryl group, an isovaleryl group, a hexanoyl group, or the like.

Examples of the "C1 to C6 alkoxycarbonyl group" may include, for example, a methoxycarbonyl group, an ethoxycarbonyl group, a tert-butoxycarbonyl group, or the like.

Examples of the "C1 to C6 alkylthio group" may include, for example, a methylthio group, an ethylthio group, a propylthio group, an isopropylthio group, or the like.

The "mono- or di-substituted C1 to C6 alkylamino group" means a C1 to C6 alkylamino group which may have one to two substituents selected from the group consisting of a halogen atom, a hydroxyl group, a cyano group, a C1 to C6 alkoxy group, a C1 to C6 alkylthio group, an amino group, a C4 to C9 cyclic amino group which may include one to three hetero atoms, a formylamino group, a C1 to C6 alkylcarbonylamino group, a C1 to C6 alkylsulfonylamino group, an arylsulfonylamino group which may be substituted, or the like.

Examples of the "C1 to C6 alkylamino group" may include, for example, a methylamino group, an ethylamino group, an n-propylamino group, an n-butylamino group, a sec-butylamino group, an n-pentylamino group, an n-hexyl amino group, or the like.

The "C4 to C9 cyclic amino group" means a cyclic amino group which contains one or more nitrogen atoms in the ring and in which an oxygen atom or a sulfur atom may also be present in the ring. Examples of the C4 to C9 cyclic amino group may include, for example, a pyrrolidyl group, a piperidyl group, a morpholyl group, an oxazolyl group, an azabicycloheptyl group, an azabicyclooctyl group, or the like.

Examples of the "C1 to C6 alkylcarbonylamino group" may include, for example, an acetylamino group, a propionylamino group, a butyrylamino group, or the like.

Examples of the "C1 to C6 alkoxycarbonylamino group" may include, for example, a methoxycarbonylamino group, an ethoxycarbonylamino group, a tert-butoxycarbonylamino group, a hexyloxycarbonylamino group, or the like.

Examples of the "C1 to C6 alkylsulfonylamino group" may include, for example, a methylsulfonylamino group, an ethylsulfonylamino group, or the like.

The "arylsulfonylamino group which may be substituted" means an arylsulfonylamino group which may have one to five substituents selected from the group consisting of a halogen atom, a hydroxyl group, a cyano group, a nitro group, a C1 to C6 alkyl group, a C1 to C6 alkoxy group and a C1 to C6 alkylthio group.

Examples of the "arylsulfonylamino group" may include, for example, a phenylsulfonylamino group, a 4-methylphenylsulfonylamino group, a naphthylsulfonylamino group, or the like.

As described in the present specification, the "C1 to C4 lower alkyl group" means a linear or branched alkyl group. Examples of the "C1 to C4 lower alkyl group" include a methyl group, an ethyl group, a propyl group, a 1-methylethyl group, a 1-methylpropyl group, a 2-methylpropan-1-yl group, a tert-butyl group, a butyl group, or the like. Among these, a methyl group or an ethyl group is preferred, with the ethyl group being more preferred.

As described in the present specification, examples of the "alkali metal" include lithium, sodium, potassium, or the like.

(Step D)

The step D is a step of subjecting an ester group (tert-butyl ester group) on one side of a diester compound represented by the general formula (IV) to ester cleavage by the addition of an acid to obtain a monocarboxylic acid compound (V).

As used in the reaction of Step D, the "acid" means an organic acid or an inorganic acid, with the organic acid being preferred.

As used in the reaction of Step D, the "organic acid" means an organic compound having an acidic functional group, such as carboxylic acid, sulfonic acid, sulfinic acid, phenol, or the like. Examples of the organic acid include formic acid, acetic acid, trifluoroacetic acid (TFA), p-toluenesulfonic acid (p-TsOH), and methanesulfonic acid.

Among these, from the viewpoint of yield, trifluoroacetic acid or formic acid is preferred, and formic acid is more preferred. In the case where formic acid is used, there are advantages that control of calorific values or isolation is easy.

As used in the reaction of Step D, the "inorganic acid" means an acid obtained in the chemical reaction of an inorganic compound. Examples of the inorganic acid include hydrochloric acid, nitric acid, phosphoric acid, sulfuric acid, hydrofluoric acid, boric acid, hydrogen chloride, or the like. Among these, hydrochloric acid is preferred.

In the case where trifluoroacetic acid or formic acid is used as an organic acid, the amount of trifluoroacetic acid or formic acid to be used is usually preferably from 10 to 100 equivalents, and more preferably from 10 to 60 equivalents, with respect to the compound represented by the general formula (IV). Further, in the case where p-toluenesulfonic acid is used as an organic acid, the amount of p-toluenesulfonic acid to be used is preferably from 0.1 to 2 equivalents, and more preferably from 0.1 to 0.5 equivalents, with respect to the compound represented by the general formula (IV).

In the case where hydrochloric acid is used as an inorganic acid, the amount of hydrochloric acid to be used is usually preferably from 1 to 100 equivalents, and more preferably from 50 to 60 equivalents, with respect to the compound represented by the general formula (IV). Further, in the case where a hydrogen chloride/ethyl acetate solution is used as an inorganic acid, the amount of the hydrogen chloride/ethyl acetate solution to be used is usually preferably from 1 to 5 equivalents, and more preferably from 1.5 to 2.5 equivalents, with respect to the compound represented by the general formula (IV).

The reaction temperature for Step D is usually preferably in the range from 0° C. to the boiling point of the solvent, more preferably from 25° C. to the boiling point of the solvent, and even more preferably from 40° C. to 50° C.

The reaction solvent for Step D is not particularly limited as long as it is stable under the reaction conditions and it is inactive and does not interfere with the reaction, or without solvent. Examples of such a solvent include hydrocarbons such as hexane, cyclohexane, heptane, or the like, aromatic hydrocarbons such as benzene, toluene, xylene, or the like, ethers such as 1,2-dimethoxyethane (DME), tetrahydrofuran (THF), diisopropylether, 2-methyltetrahydrofuran, tetrahydropyran, diglyme, cyclopentylmethylether, or the like, esters such as methyl acetate, ethyl acetate, isopropyl acetate, butyl acetate, or the like, nitriles such as acetonitrile, propionitrile, or the like, alcohols such as methanol, ethanol, 2-propanol, tert-butyl alcohol, 2-methoxyethanol, ethylene glycol, diethylene glycol, or the like, halogenated hydrocarbons such as dichloromethane, chloroform, 1,2-dichloroethane, 1,1,1,3,3-pentafluorobutane, or the like, and amides such as N,N-dimethylformamide (DMF), N,N-dimethylacetamide, N-methylpyrrolidone, or the like.

These solvents are properly selected depending on the ease of initiating the reaction, and used either alone or in combination. Further, the solvent may be used as a non-aqueous solvent, using a proper dehydrating agent or desiccant, as desired.

In Step D, in the case where formic acid is used as an acid, it is preferable to carry out the reaction in the absence of a solvent, while in the case where the reaction is carried out using other organic acids, the solvent is preferably acetonitrile or toluene, and more preferably toluene.

(Step C)

Step C is a step of condensing the monocarboxylic acid compound represented by the general formula (V) with an amine represented by the general formula (VI) to obtain an amide compound represented by the general formula (III). For the condensing reaction, the condensing conditions which are generally used may be used.

[Chem. 17]

$$R^1\text{—}NH_2 \qquad (VI)$$

In the formula (VI), $R^1$ has the same meaning as described above.

The amount of the amine represented by the general formula (VI) to be used is not particularly limited, and is usually preferably from 1 to 3 equivalents, and more preferably from 1.0 to 1.5 equivalents, with respect to the compound represented by the general formula (V).

It is preferable to use a condensing agent in the reaction of Step C. The condensing agent is not particularly limited as long as an amide bond can be produced from a carboxylic acid and an amine.

Examples of the condensing agent include 1-ethyl-3-(3-dimethylaminopropyl)carbodiimide (EDCI) or a hydrochloride thereof, dicyclohexylcarbodiimide (DCC), diisopropylcarbodiimide (DIPC), diphenylphosphorylazide (DPPA), diethyl cyanophosphate (DEPC), benzotriazol-1-yl-oxytrisdimethylaminophosphonium hexafluorophosphate (BOP), 2-(1-hydrobenzotriazol-1-yl)-1,1,3,3-tetramethyluronium hexafluorophosphate (HBTU), 2-(1-hydrobenzotriazol-1-yl)-1,1,3,3-tetramethyluroniumtetrafluoroborate (TBTU), 2-chloro-N,N,2-trimethylpropenylamine, 2-chloro-4,6-dimethoxy-1,3,5-triazine (CDMT), 4-(5,6-dimethoxy-1,3,5-triazin-2-yl)-4-methylmorpholine hydrochloride (DMTMM), 2-chloro-1-methylpyridinium iodide (CMPI), or the like.

Among these, 1-ethyl-3-(3-dimethylaminopropyl)carbodiimide (EDCI) or a hydrochloride thereof is preferred, and 1-ethyl-3-(3-dimethylaminopropyl)carbodiimide hydrochloride (EDCI.HCl) is more preferred.

The amount of the condensing agent to be used is not particularly limited, and is usually preferably from 1 to 5 equivalents, and more preferably from 1.0 to 1.5 equivalents, with respect to the compound represented by the general formula (V).

In the reaction of Step C, an additive is preferably used since the reaction yield is enhanced when the condensing agent is used together with an additive.

Examples of the additive include 1-hydroxybenzotriazole (HOBt), 1-hydroxy-7-azabenzotriazole (HOAt), 1-hydroxysuccinimide (HOSu), and 3,4-dihydro-3-hydroxy-4-oxobenzotriazine (HOOBt). Among these, 1-hydroxysuccinimide (HOSu) or 1-hydroxybenzotriazole (HOBt) is preferred, and 1-hydroxybenzotriazole (HOBt) is more preferred.

The amount of the additive to be used is not particularly limited, and the reaction yield can be maintained even in the case where it is decreased to 0.01 equivalents with respect to the compound represented by the general formula (V). The amount of the additive to be used is preferably from 0.01 to 5 equivalents, and more preferably from 0.01 to 1.2 equivalents.

In Step C, the reaction proceeds even without use of a base, but the use of the condensing agent together with a base increases the reaction conversion rate, which is thus preferable.

The base may be any one which does not interfere with the reaction, and examples thereof include organic bases such as triethylamine, trimethylamine, tripropylamine, diisopropyl ethylamine, pyridine, dimethylaniline, N-methylmorpholine, N-methylpyrrolidine, and 4-dimethylaminopyridine.

Among these, N-methylmorpholine, N-methylpyrrolidine, or triethylamine is preferred, and triethylamine is more preferred.

For the reaction of Step C, it is usually preferable to use a solvent. Examples of the solvent include esters such as ethyl acetate, butyl acetate, isopropyl acetate, or the like, aromatic compounds such as benzene, toluene, xylene, or the like, hydrocarbons such as hexane, heptane or cyclohexane, or the like, ethers such as dioxane, tetrahydrofuran (THF), 2-methyltetrahydrofuran (2-MeTHF), tert-butyl methyl ether (TBME), dimethoxyethane (DME), diglyme, or the like, halogenated hydrocarbons such as dichloromethane, chloroform, carbon tetrachloride, 1,2-dichloroethane, or the like, nitriles such as acetonitrile or the like, amides such as N,N-dimethylformamide (DMF), N,N-dimethylacetamide, N-methylpyrrolidone, or the like, water, or a mixture thereof.

Among these, tetrahydrofuran, a mixed solvent of tetrahydrofuran and N,N-dimethylformamide, or a mixed solvent of 2-methyltetrahydrofuran and N,N-dimethylformamide is preferred, and tetrahydrofuran is more preferred.

The reaction temperature of Step C is usually preferably in the range from −20° C. to the boiling point of the solvent to be used, more preferably in the range from 0° C. to the boiling point of the solvent, and even more preferably from 30° C. to 50° C.

(Step B)

Step B is a step of treating the amide compound represented by the general formula (III) with a base to obtain a 4-oxopyrrolidine-3-carboxamide derivative represented by the general formula (I).

Examples of the base include an alkali metal carbonate, an alkali metal amide, and an alkali metal alkoxide, or an alkali metal hydride. Among these, alkali metal alkoxides are preferred.

The "alkali metal carbonate" means a carbonate of an alkali metal. Examples of the alkali metal carbonate include lithium carbonate, sodium carbonate, and potassium carbonate, and potassium carbonate is preferred.

The "alkali metal amide" refers to a compound formed by substituting a hydrogen atom of an amine with a metal atom. Examples of the alkali metal amide include lithium amide, sodium amide, potassium amide, lithium diethylamide, lithium diisopropylamide, lithium cyclohexylisopropylamide, lithium tetramethylpiperizide, lithium hexamethyl disilazide (LHMDS), sodium hexamethyl disilazide (NaHMDS), and potassium hexamethyl disilazide (KHMDS). Among these, potassium hexamethyl disilazide is preferred.

The "alkali metal alkoxide" refers to a compound formed by substituting a hydroxyl group of an alcohol with an alkali metal. Examples of the alkali metal alkoxide include sodiummethoxide (NaOMe), sodiumethoxide (NaOEt), potassiumethoxide (KOEt), sodium tert-butoxide (tBuONa), potassium tert-butoxide (tBuOK), lithium tert-butoxide (tBuOLi), sodium tert-pentoxide ($C_2H_5C(CH_3)_2ONa$), potassium tert-pentoxide ($C_2H_5C(CH_3)_2OK$) or the like.

Among these, potassium tert-butoxide, sodium tert-pentoxide, or potassium tert-pentoxide is preferred, and potassium tert-pentoxide is more preferred.

Examples of the "alkali metal hydride" include lithium hydride, sodium hydride, potassium hydride, or the like.

The amount of the base to be used is not particularly limited, and is usually preferably from 1 to 4 equivalents, with respect to the compound represented by the general formula (III), and from the viewpoint of suppression of production of side-products represented by the general formula (VII), it is more preferably from 1 to 1.5 equivalents.

[Chem. 18]

(VII)

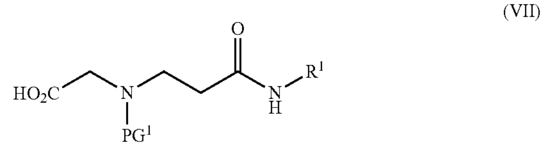

In the general formula (VII), $PG^1$ and $R^1$ have the same meanings as described above.

The reaction temperature of Step B is usually preferably in the range from −20° C. to 100° C., and from the viewpoint of the suppression of production of side-products represented by the general formula (VII), it is more preferably from 35° C. to 55° C., and even more preferably from 40° C. to 50° C.

For the reaction of Step B, it is usually preferable to use a solvent. Examples of the solvent include alcohols such as methanol, ethanol, 2-propanol, tert-butyl alcohol, 2-methoxyethanol, ethylene glycol, diethylene glycol, or the like, esters such as ethyl acetate, butyl acetate, or the like, aromatic compounds such as benzene, toluene, xylene, or the like, hydrocarbons such as hexane, heptane, cyclohexane, or the like, ethers such as dioxane, tetrahydrofuran, 2-methyltetrahydrofuran, dimethoxyethane, digylme, or the like, halogenated hydrocarbons such as dichloromethane, chloroform, carbon tetrachloride, 1,2-dichloroethane, or the like, nitriles such as acetonitrile or the like, amides such as N,N-dimethylformamide (DMF), N,N-dimethylacetamide, N-methylpyrrolidone, or the like, and a mixture thereof.

Among these, N,N-dimethylformamide, tetrahydrofuran, or toluene is preferred, and toluene is more preferred.

(Step A)

Step A is a step of subjecting a racemic form (I) of a 4-oxopyrrolidine-3-carboxamide derivative to asymmetric hydrogenation using an optically active catalyst to obtain an optically active form (II) of an anti-(3S,4R)-4-hydroxypyrrolidine-3-carboxamide derivative or it's enantiomer.

The "optically active catalyst" is an optically active transition metal compound obtained by mixing a transition metal compound with an optically active chiral ligand in an organic solvent.

Examples of the transition metal compound include a ruthenium compound, a rhodium compound, an iridium compound, a nickel compound, a palladium compound, a platinum compound, or the like, and a ruthenium compound is preferred.

Examples of the ruthenium compound include dichloro(p-cemene)ruthenium(II) dimer, a dibromo(p-cemene)ruthenium(II) dimer, a diiodo(p-cemene)ruthenium(II) dimer, a dichloro(1,5-cyclooctadiene)ruthenium(II) polymer, a dichlorobenzeneruthenium(II) dimer, a dibromobenzeneruthenium(II) dimer, a diiodobenzeneruthenium(II) dimer, or the like. Among these, a dichlorobenzeneruthenium(II) dimer is preferred.

As the chiral ligand, a chiral ligand which is usually used can be used. Examples thereof include the ligands described in CATALYTIC ASYMMETRIC SYNTHESIS, Second Edition, 2000, WILEY-VCH, p. 2 to 6.

Examples of the chiral ligand include C2-chiraldiphosphines such as (5)-BINAP, (S)-TolBINAP, (S)-XylBINAP, (S)-Cy-BINAP, (S)-H8-BINAP, (S)-MeO-BIPHEP, (S)-p-Tol-MeO-BIPHEP, di-t-Bu-MeO-BIPHEP, (S)-SEGPHOS, (S)-DM-SEGPHOS, (S)-DTBM-SEGPHOS, (S)-QUINAP, (S,S)-BDPP, (S)-BIPHEMP, (S)-Me-BPE, (S,S)-DIOP, (S,S)-DIOP-OH, (S,S)-DIPAMP, (S)-SYNPHOS, (S,S)-CHIRAPHOS, (S,S)-Me-DuPHOS, or the like, and their enantiomers, or non-C2-chiraldiphosphines such as (R)-(S)-BPPFA, (R)—(S)-BPPFOH, (2S,4S)-BPPM, (R)-(S)-JOSIPHOS, (R)—(S)-XYLIPHOS, (R)-PROPHOS, (R)-MeO-MOP, or the like, and enantiomers thereof.

Among these, (S)-BINAP, (S)-TolBINAP, (S)-MeO-BIPHEP, (S)-SEGPHOS, (S)-DM-SEGPHOS, or their enantiomers are preferred, and (S)-BINAP or it's enantiomer is more preferred.

BINAP means 2,2'-bis(diphenylphosphino)-1,1'-binaphthyl.

SEGPHOS means 5,5'-bis(diphenylphosphino)-4,4'-bi-1,3-benzodioxole.

DM-SEGPHOS means 5,5'-bis(di(3,5-xylyl)phosphino)-4,4'-bi-1,3-benzodioxole.

TolBINAP means 2,2'-bis(di-p-tolylphosphino)-1,1'-binaphthyl.

MeO-BIPHEP means (6,6'-dimethoxybiphenyl-2,2'-diyl) bis(diphenylphosphine).

The BINAP analogue means a compound each having 1 to 5 substituents such as an alkyl group or the like in 4 benzene rings on phosphorous atoms of BINAP, a compound having a substituent such as an alkyl group and an aryl group on a naphthyl ring of BINAP, a compound having a naphthyl ring partially hydrogenated, or the like. Examples of the BINAP analogue include (S)-TolBINAP, (S)-XylBINAP, (S)-Cy-BINAP, (S)-H8-BINAP, or the like.

The SEGHOPS analogue means a compound each having 1 to 5 substituents such as an alkyl group, an alkoxy group, or the like in 4 benzene rings on phosphorous atoms of SEGHOPS. Examples of the SEGHOPS analogue include (S)-DM-SEGPHOS, (S)-DTBM-SEGPHOS, or the like.

The MeO-BIPHEP analogue means a compound each having 1 to 5 substituents such as an alkyl group or the like in 4 benzene rings on phosphorous atoms of MeO-BIPHEP. Examples of the MeO-BIPHEP analogue include (S)-p-Tol-MeO-BIPHEP, di-tert-Bu-MeO-BIPHEP, or the like.

The optically active catalyst may be any optically active transition metal compound which is obtained by mixing a transition metal compound with an optically active chiral ligand in an organic solvent. Examples of the optically active catalyst include a ruthenium-(S)-BINAP catalyst produced from a ruthenium compound and an (S)-BINAP, a ruthenium-(S)-SEGPHOS catalyst produced from a ruthenium compound and (S)-SEGPHOS, a ruthenium-(S)-MeO-BIPHEP catalyst produced from a ruthenium compound and (S)-MeO-BIPHEP, and a ruthenium-(S)-DM-SEGPHOS catalyst produced from a ruthenium compound and (S)-DM-SEGPHOS. Among these, a ruthenium-(S)-BINAP catalyst is preferred.

The amount of the optically active catalyst to be used is not particularly limited, and is usually preferably from 0.01 to 20 mol %, more preferably from 0.01 to 2 mol %, and even more preferably from 0.01 to 1 mol %, with respect to that of the compound represented by the general formula (I). In the reaction of Step A, even in the case where the amount of the optically active catalyst to be used is decreased to 0.1 mol %, the reaction proceeds while not affecting the yield or the stereoselectivity of a desired product.

In the case where the amount of the optically active catalyst is large, a transition metal compound or the like remains in the compound represented by the general formula (II), which is a desired product, and purification is difficult, and the optically active catalyst is expensive. Therefore, a smaller amount of the optically active catalyst to be used is more preferred.

Examples of the hydrogen source include hydrogen or formic acid/triethylamines, formic acid/α-phenethylamines, formic acid/triphenylamines, ammonium formate, cyclohexenes, 2-propanol, or the like, and hydrogen is preferred.

For the reaction of Step A, it is usually preferable to use a solvent. Examples of the solvent include water, organic acids such as formic acid, acetic acid, or the like, esters such as ethyl acetate, butyl acetate, or the like, aromatic compounds such as benzene, toluene, chlorobenzene, xylene, or the like, hydrocarbons such as hexane, heptane, cyclohexane, or the like, alcohols such as methanol, ethanol, 2,2,2-trifluoroethanol ($CF_3CH_2OH$), 2-propanol (2-PrOH), tert-butyl alcohol, ethylene glycol, diethylene glycol, or the like, ethers such as dioxane, tetrahydrofuran, dimethoxyethane, diglyme, or the like, halogenated hydrocarbons such as dichloromethane, chloroform, carbon tetrachloride, 1,2-dichloroethane, or the like, amides such as N,N-dimethylformamide (DMF), N,N-dimethylacetamide, N-methylpyrrolidone, and a mixture thereof.

Among these, dichloromethane, tetrahydrofuran, ethyl acetate, toluene, xylene, or chlorobenzene is preferred, and dichloromethane or chlorobenzene is more preferred.

The reaction temperature is usually preferably in the range of from −20° C. to 200° C., more preferably in the range of from 25° C. to 120° C., even more preferably in the range of from 60° C. to 100° C., and particularly preferably in the range of from 60° C. to 80° C.

The reaction pressure is not particularly limited, and the reaction can be usually carried out under the conditions of from ordinary pressure to 10 MPa. In the reaction of Step A, even in the case where the reaction is carried out under the condition of low pressures of from 0.1 to 1 MPa, the reaction proceeds while not affecting the yield or the stereoselectivity of a desired product. The reaction under the high pressure condition is not industrially suitable and has a high risk of explosion, and therefore, a lower reaction pressure is preferred. In the present reaction, the preferable reaction pressure is from 0.1 to 1 MPa.

After the reaction of Step A ends, the compound of the general formula (II) can be isolated by purifying, as desired, with a general separation means (for example, extraction, recrystallization, chromatography, or the like).

Particularly by carrying out recrystallization, in the reaction of Step A, it is possible to remove enantiomers and diastereomers (syn-forms) of the desired products which are produced in a small amount, thereby obtaining an optically pure anti-4-hydroxypyrrolidine-3-carboxamide derivative. Further, in the case where the amount of an optically active catalyst to be used is 0.1 mol % or less, a purification operation other than recrystallization is not required for removal of residual metals.

The reaction of Step A is an excellent production method in that the reaction can be carried out under a low pressure condition, the amount of an expensive optically active catalyst to be used can be decreased, and the purification is easy by controlling the amount of the optically active catalyst to be used, as compared with methods in the prior art using an asymmetric hydrogenation reaction of an α-substituted β-ketoester derivative (International Publication WO 2007/102567).

Furthermore, the reaction of Step A is an example of catalytic asymmetric hydrogenation using an α-substituted β-ketoamide derivative as a substrate, but thereby obtaining a desired product, an anti-β-hydroxyamide derivative, as a main product. Although an example of catalytic asymmetric hydrogenation using α-substituted β-ketoamide can be found in Organic Letters, 2010, 12(3), 512-515, a syn-β-hydroxyamide form is provided as a main product, which is totally different from the present reaction for providing an anti-β-hydroxyamide form as a main product.

EXAMPLES

Next, the present invention will be described with reference to Examples, but the present invention is not limited to these Examples.

In Examples, Reference Examples, and Comparative Examples, "-fold amount" means an amount (mL) of a solvent with respect to the mass (g) of a substrate.

Reference Example 1 tert-Butyl 3-{N-benzyloxycarbonyl-N-(ethoxycarbonylmethyl)amino}propionate

To glycine ethyl ester hydrochloride (163 g, 1.17 mol) were put a 3:1 mixed solvent of 2-propanol and water (600 mL), followed by warming the mixture and triethylamine (174 mL, 1.25 mol) was added thereto at an internal temperature of 59° C. To the mixed liquid was added dropwise tert-butyl acrylate (50.0 g, 0.390 mol) at an internal temperature of from 60° C. to 62° C., followed by stirring at an internal temperature of from 60° C. to 62° C. for 2 hours. Furthermore, to the mixed liquid was added dropwise tert-butyl acrylate (50.0 g, 0.390 mol) at an internal temperature of from 62° C. to 63° C., followed by stirring at an internal temperature of from 60° C. to 62° C. for 5 hours.

The reaction mixture was cooled to room temperature and was allowed to stand overnight. The reaction mixture was diluted by the addition of ethyl acetate (1 L), and extracted by the addition of 3% sodium hydrogen carbonate (1 L). The organic layer was collected by separation to obtain a solution of tert-butyl 3-(ethoxycarbonylmethylamino)propionate in ethyl acetate. The product was partially concentrated and $^{1}H$ NMR was measured.

$^{1}H$ NMR (400 MHz, $CDCl_3$) δ: 1.28 (3H, t, J=7.2 Hz), 1.45 (9H, s), 2.44 (2H, t, J=6.6 Hz), 2.87 (2H, t, J=6.6 Hz), 3.41 (2H, s), 4.20 (2H, q, J=7.1 Hz).

To the total amount of the solution of tert-butyl 3-(ethoxycarbonylmethylamino)propionate in ethyl acetate was added a sodium hydrogen carbonate solution (72.1 g (0.860 mol) of sodium hydrogen carbonate was dissolved in 1.3 L of water) at approximately room temperature, and benzyl chloroformate (133 g, 0.780 mol) was added dropwise at an internal temperature of from 26° C. to 33° C., followed by stirring at an internal temperature of from 28° C. to 33° C. for 2 hours.

The reaction mixture was cooled to room temperature and allowed to stand overnight and then extracted. The organic layer was collected by separation, and the organic layer was sequentially washed with 0.5 mol/L hydrochloric acid (0.5 L) and 5% brine (0.5 L), and dried over anhydrous sodium sulfate. The insoluble materials were separated by filtration and the filtrate was concentrated under reduced pressure to obtain 265 g of a title compound as yellow oil.

$^{1}H$ NMR (400 MHz, $CDCl_3$) δ: 1.23 (3H, dt, J=29.3, 7.3 Hz), 1.43 (9H, s), 2.56 (2H, dt, J=22.5, 6.4 Hz), 3.56-3.64 (2H, m), 4.05-4.21 (4H, m), 5.11-5.17 (2H, m), 7.29-7.38 (5H, m).

The reaction conversion rates of Examples 1 to 3 in Table 1 are values calculated as follows, by carrying out HPLC measurement using the measurement condition A below and taking the area percentages (%) of the obtained substrate and desired product to give a total percentage of 100%.

$$\text{Reaction conversion rate(\%)} = \text{Desired product}/(\text{Substrate}+\text{Desired product})\times 100$$

The substrate refers to tert-butyl 3-{N-benzyloxycarbonyl-N-(ethoxycarbonylmethyl)amino}propionate and the desired product refers to 3-{N-benzyloxycarbonyl-N-(ethoxycarbonylmethyl)amino}propionic acid, respectively.

Measurement Condition A

Column; Chemicals Evaluation and Research Institute, CERI L-column2 ODS, 4.6ϕ×150 mm, 3 μm), pre-column: Chemicals Evaluation and Research Institute, CERI L-column2 ODS, 4.0ϕ×10 mm, mobile phase: Solution A: methanol, Solution B: phosphate buffer (pH 6.9), 0 to 5 minutes; A:B=53:47 (isocratic), 5 to 15 minutes; A:B=53:47→75:25 (linear gradient), 15 to 40 minutes; A:B=75:25 (isocratic), detection wavelength: 210 nm, column temperature: 40° C., flow rate: 0.80 mL/min.

Retention time: substrate; approximately 32 minutes, desired product; approximately 6 minutes The reaction conversion rates of Examples 4 to 7 in Table 1 are values calculated as follows, by carrying out HPLC measurement using the measurement condition B below and taking the area percentages (%) of the obtained substrate and desired product to give a total percentage of 100%.

$$\text{Reaction conversion rate(\%)} = \text{Desired product}/(\text{Substrate}+\text{Desired product})\times 100$$

The substrate refers to tert-butyl 3-{N-benzyloxycarbonyl-N-(ethoxycarbonylmethyl)amino}propionate and the desired product refers to 3-{N-benzyloxycarbonyl-N-(ethoxycarbonylmethyl)amino}propionic acid, respectively.

Measurement Condition B

Column; GL Sciences Inc., Inertsil ODS-3 (4.6ϕ×150 mm), pre-column; GL Sciences Inc., Inertsil ODS-3 (4.0ϕ×10 mm), mobile phase; Solution A: acetonitrile, Solution B: diluted phosphoric acid (1→1000) solution, 0 to 25 minutes; A:B=60:40 (isocratic), detection wavelength: 210 nm, column temperature: 40° C., flow rate: 1.0 mL/min.

Retention time: substrate; approximately 3 minutes, desired product; approximately 14 minutes

Example 1

3-{N-Benzyloxycarbonyl-N-(ethoxycarbonylmethyl)amino}propionic acid

To tert-butyl 3-{N-benzyloxycarbonyl-N-(ethoxycarbonylmethyl)amino}propionate (500 mg, 1.37 mmol) was added formic acid (2.5 mL, 66.3 mmol), followed by stirring at an outer temperature set of 40° C. for 3 hours. After leaving to be cooled, to the reaction mixture were added ethyl acetate (10 mL) and water (10 mL), and the organic layer was collected by separation. To the aqueous layer was added ethyl acetate (10 mL), the organic layer was collected by separation, and then the organic layer was combined, washed with saturated brine (10 mL), then dried over anhydrous sodium sulfate, and concentrated under reduced pressure. The obtained concentrated residue was dried at room temperature under reduced pressure to obtain 421 mg (yield 99%) of a title compound as colorless oil.

Examples 2 to 7

The reactions were carried out under the conditions described in Table 1 using tert-butyl 3-{N-benzyloxycarbonyl-N-(ethoxycarbonylmethyl)amino}propionate, and the HPLC measurement of the reaction mixture was carried out. The results are shown in Table 1.

| | Reaction condition | Reaction conversion rate (%) | Yield (%) |
|---|---|---|---|
| Example 1 | $HCO_2H$ (48.4 equivalents), 35° C. to 45° C. | 99.3 | 99 |
| Example 2 | TFA (24.6 equivalents), $CH_2Cl_2$ (5-fold amount), 30° C. | 100 | Quantitative |
| Example 3 | p-TsOH•$H_2O$ (0.1 equivalents), Toluene (5-fold amount), reflux | 100 | 81 |
| Example 4 | p-TsOH•$H_2O$ (1.5 equivalents), acetonitrile (10-fold amount), room temperature | 86.2 | — |
| Example 5 | Hydrogen chloride/ethyl acetate (2.0 equivalents), room temperature | 84.2 | — |
| Example 6 | Hydrochloric acid (58.1 equivalents), 2-PrOH (5-fold amount), room temperature | 97.3 | — |
| Example 7 | Hydrochloric acid (58.1 equivalents), THF (5-fold amount), room temperature | 98.2 | — |

In any case of the reaction conditions shown in Table 1, the reaction of Step D proceeded, thereby obtaining a desired product (Examples 1 to 7). Particularly, in the case of using formic acid and trifluoroacetic acid as an acid, the reaction of Step D proceeded smoothly, thereby obtaining a desired product in high yield (Examples 1 and 2).

In Tables 2 to 4, the reaction conversion rate refers to a value calculated as follows, by carrying out HPLC measurement using the measurement condition C below and taking the area percentages (%) of the obtained substrate and desired product to give a total percentage of 100%.

Reaction conversion rate(%)=Desired product/(Substrate+Desired product)×100

The substrate refers to 3-{N-benzyloxycarbonyl-N-(ethoxycarbonylmethyl)amino}propionic acid and the desired product refers to ethyl N-benzyloxycarbonyl-N-{(2-cyclopropylaminocarbonyl)ethyl}aminoacetate, respectively.

Measurement Condition C

Column; GL Sciences Inc., Inertsil ODS-3 (4.6ϕ×150 mm), pre-column; GL Sciences Inc., Inertsil ODS-3 (4.0ϕ×10 mm), mobile phase; Solution A: acetonitrile, Solution B: diluted phosphoric acid (1→1000) solution, 0 to 25 minutes; A:B=60:40 (isocratic), detection wavelength: 210 nm, column temperature: 40° C., flow rate: 1.0 mL/min.

Retention time: substrate; approximately 22 minutes, desired product; approximately 25 minutes Example 8

Ethyl N-benzyloxycarbonyl-N-{(2-cyclopropylaminocarbonyl)ethyl}aminoacetate

To 3-{N-benzyloxycarbonyl-N-(ethoxycarbonylmethyl)amino}propionic acid (866 mg, equivalent to 2.83 mmol) were added THF (17 mL), followed by dissolution. HOBt.$H_2O$ (521 mg, 3.40 mmol), cyclopropylamine (0.49 mL, 7.08 mmol), and EDCI.HCl (652 mg, 3.40 mmol) were sequentially added thereto, followed by stirring at room temperature for 1 hour.

After being allowed to stand at room temperature overnight, 2 mol/L hydrochloric acid (10 mL) and ethyl acetate (20 mL) were added to the reaction mixture, and the organic layer was collected by separation. To the aqueous layer was added ethyl acetate (20 mL), the organic layer was collected by separation, and then the organic layer was combined, sequentially washed with water (20 mL), saturated sodium hydrogen carbonate (20 mL), water (20 mL), and saturated brine (20 mL), and then dried over anhydrous sodium sulfate.

After concentrating under reduced pressure, the concentrated residue was purified by silica gel column chromatography (Kanto Chemical Co., Inc.) Si60 (spherical), eluent: ethyl acetate), and dried at room temperature under reduced pressure to obtain 712 mg (yield 72%) of a title compound as a white solid.

Examples 9 to 16

By the same methods as in Example 8, the reaction was carried out at room temperature using cyclopropylamine (1.1 to 2.5 equivalents) and HOBt.$H_2O$(0 to 1.2 equivalents) in the amounts shown in Table 2 and a 2:1 mixed solvent (20-fold amount) of THF/DMF or 2-MeTHF/DMF as a reaction solvent.

Subsequently, the HPLC measurement of the reaction mixture was carried out and a desired product was purified and isolated by silica gel column chromatography. The results are shown in Table 2.

TABLE 2

| | Cyclopropyl amine (equivalents) | HOBt•$H_2O$ (equivalents) | Solvent | Reaction conversion rate (%) | Yield (%) |
|---|---|---|---|---|---|
| Example 8 | 2.5 | 1.2 | THF | 100 | 72 |
| Example 9 | 2.5 | 1.2 | THF/DMF | 100 | 68 |
| Example 10 | 2.5 | 0.1 | THF/DMF | 100 | 73 |
| Example 11 | 2.5 | 0.1 | 2-MeTHF/DMF | 100 | 71 |
| Example 12 | 2.5 | 0.05 | 2-MeTHF/DMF | 100 | 69 |
| Example 13 | 2.5 | 0.01 | 2-MeTHF/DMF | 100 | 68 |
| Example 14 | 2.5 | 0 | 2-MeTHF/DMF | 100 | 56 |
| Example 15 | 2.1 | 0.05 | 2-MeTHF/DMF | 100 | 70 |
| Example 16 | 1.1 | 0.05 | 2-MeTHF/DMF | 100 | 83 |

Under all the reaction conditions shown in Table 2, the reaction of Step C was carried out smoothly (Examples 8 to 16). Even when HOBt.$H_2O$ as an additive was not added, the reaction of Step C proceeds (Example 14), but in the case where 0.01 to 0.1 equivalents of HOBt.$H_2O$ was added, a desired product was obtained in excellent yield (Examples 11 to 13). Further, it became clear that the equivalents of cyclopropylamine as an amine can be decreased to 1.1 equivalents (Example 16).

Examples 17 to 20

To 3-{N-benzyloxycarbonyl-N-(ethoxycarbonylmethyl)amino}propionic acid (corresponding to 100 mg, 0.311 mmol) was added THF (0.5 mL), followed by dissolution. HOBt.$H_2O$(2.39 mg, 0.0156 mmol), a base shown in Table 3 (1.1 equivalents), cyclopropylamine (23.7 μL, 0.342 mmol), and EDCI.HCl (71.5 mg, 0.373 mmol) were sequentially added thereto, followed by stirring at an outer temperature set of 40° C. for 1 hour. Then, the HPLC measurement of this reaction mixture was carried out. The results are shown in Table 3.

TABLE 3

| | Base | Reaction conversion rate (%) |
|---|---|---|
| Example 17 | Triethylamine | 100 |
| Example 18 | N-Methylpyrrolidine | 87.5 |
| Example 19 | N-Methylmorpholine | 97.5 |
| Example 20 | — | 97.5 |

Under all the reaction conditions shown in Table 3, the reaction of Step C proceeded (Examples 17 to 20). Even when the base was not added, the reaction of Step C proceeds (Example 20), but in the case where the base was added, the reaction conversion rate was improved (Examples 17 to 19). In particular, in the case where triethylamine was added as a base, the reaction conversion rate was highest (Example 17).

Examples 21 to 29

To 3-{N-benzyloxycarbonyl-N-(ethoxycarbonylmethyl) amino}propionic acid (corresponding to 100 mg, 0.311 mmol) was added the solvent shown in Table 4 (0.5 mL), followed by dissolution. HOBt.$H_2O$ (2.39 mg, 0.0156 mmol), triethylamine (47.4 μL, 0.342 mmol), cyclopropylamine (23.7 μL, 0.342 mmol), and EDCI.HCl (71.5 mg, 0.373 mmol) were sequentially added thereto, followed by stirring at an outer temperature set of 40° C. for 1 to 4.5 hours. The HPLC measurement of this reaction mixture was carried out. The results are shown in Table 4.

TABLE 4

| | Solvent | Reaction conversion rate (%) | Reaction hours (hours) |
|---|---|---|---|
| Example 17 | THF | 100 | 1 |
| Example 21 | 2-MeTHF | 94.6 | 2 |
| Example 22 | 2-MeTHF/DMF | 96.7 | 2 |
| Example 23 | TBME | 95.7 | 2 |
| Example 24 | DME | 92.3 | 2 |
| Example 25 | Toluene | 95.4 | 2 |
| Example 26 | Isopropyl acetate | 89.5 | 2 |
| Example 27 | DME:$H_2O$ = 15:1 | 83.5 | 1.5 |
| Example 28 | DME:$H_2O$ = 20:1 | 94.0 | 4.5 |
| Example 29 | THF:$H_2O$ = 9:1 | 91.9 | 4.5 |

Under all the reaction conditions shown in Table 4, the reaction of Step C proceeded (Examples 17, 21 to 29). In particular, in the case where THF was used as a solvent, the reaction conversion rate was highest (Example 17).

In Tables 5 to 6, HPLC (%) refers to a value calculated as follows, by carrying out HPLC measurement using the measurement condition D below and taking the area percentages (%) of the obtained substrate, desired product, and hydrolyzed products to give a total percentage of 100%.

Area Percentage of Each Component(%)=(Area Value of Each Component)/(Total Area Value of Each Component)×100

The substrate refers to ethyl N-benzyloxycarbonyl-N-{(2-cyclopropylaminocarbonyl)ethyl}aminoacetate, the desired product refers to benzyl 3-(cyclopropylcarbamoyl)-4-oxopyrrolidine-1-carboxylate, and the hydrolyzed product refers to N-benzyloxycarbonyl-N-{(2-cyclopropylaminocarbonyl) ethyl}aminoacetic acid, respectively.

Measurement Condition D

Column; GL Sciences Inc., Inertsil ODS-3 (4.6ϕ×150 mm), pre-column; GL Sciences Inc., Inertsil ODS-3 (4.0ϕ×10 mm), mobile phase; Solution A: acetonitrile, Solution B: diluted phosphoric acid (1→1000) solution, 0 to 25 minutes; A:B=38:62 (isocratic), detection wavelength: 210 nm, column temperature: 40° C., flow rate: 1.0 mL/min.

Retention time: substrate; approximately 21 minutes, desired product; approximately 13 minutes, and hydrolyzed products: approximately 6 minutes Example 30

Benzyl 3-(cyclopropylcarbamoyl)-4-oxopyrrolidine-1-carboxylate

To a solution of ethyl N-benzyloxycarbonyl-N-{(2-cyclopropylaminocarbonyl)ethyl}aminoacetate (200 mg, 0.574 mmol) in toluene (2.0 mL) was added potassium tert-butoxide (136 mg, 1.21 mmol) as a base at an outer temperature set of 40° C., followed by stirring for 2 hours. Then, the HPLC measurement of this reaction mixture was carried out. The results are shown in Table 5.

Examples 31 to 40

By the same method as in Example 30, the bases (2.1 equivalents) and the solvent (10-fold amount), described in Table 5, were stirred at an outer temperature set of 40° C. for 0.5 to 7 hours. Then, the HPLC measurement of this reaction mixture was carried out. The results are shown in Table 5.

TABLE 5

| | Base | Solvent | Substrate:desired product:hydrolyzed product (HPLC %) |
|---|---|---|---|
| Example 30 | tBuOK | Toluene | 0:83.3:16.7 |
| Example 31 | tBuONa | Toluene | 0:55.0:45.0 |
| Example 32 | tBuOLi | Toluene | 40.0:52.1:7.9 |
| Example 33 | KHMDS | Toluene | 0:61.3:38.7 |
| Example 34 | NaHMDS | Toluene | 0:87.6:12.4 |
| Example 35 | LHMDS | Toluene | 0:84.5:15.5 |
| Example 36 | NaH | THF | 0:87.0:13.0 |
| Example 37 | NaOMe | Methanol | 0.7:70.7:28.6 |
| Example 38 | NaOMe | Toluene | 81.3:7.7:11.0 |
| Example 39 | $C_2H_5C(CH_3)_2OK$ | Toluene | 0:94.2:5.8 |
| Example 40 | $C_2H_5C(CH_3)_2ONa$ | Toluene | 0:74.6:25.4 |

Under all the reaction conditions shown in Table 5, desired products could be obtained by the reaction of Step B (Examples 30 to 40). Particularly, in the case where potassium tert-butoxide, sodium tert-butoxide, potassium hexamethyl disilazide, sodium hexamethyl disilazide, lithium hexamethyl disilazide, sodium hydride, or sodium tert-pentoxide was used as a base, hydrolyzed products were generated as side-products, but the reaction could be completed (Examples 30, 31,33 to 36, and 40).

Furthermore, in the case where potassium tert-pentoxide was used as a base, the side production of hydrolyzed products could be suppressed to less than 10%, and further, the reaction could be completed (Example 39).

Example 41

Benzyl 3-(cyclopropylcarbamoyl)-4-oxopyrrolidine-1-carboxylate

To a solution of ethyl N-benzyloxycarbonyl-N-{(2-cyclopropylaminocarbonyl)ethyl}aminoacetate (500 mg, 1.44 mmol) in toluene (5.0 mL) was added a 1.7 mol/L solution (2.6 mL, 4.46 mmol) of potassium tert-pentoxide in toluene at an outer temperature set of 40° C., followed by stirring for 2 hours.

The reaction mixture was ice-cooled, 2 mol/L hydrochloric acid (10 mL) and ethyl acetate (20 mL) were added thereto, and the organic layer was collected by separation. To the aqueous layer was added ethyl acetate (20 mL), the organic layer was collected by separation, and then the organic layer was combined and washed with saturated brine (20 mL).

After drying over anhydrous sodium sulfate and then concentrating under reduced pressure, the concentrated residue was purified by silica gel column chromatography (Kanto Chemical Co., Inc. Si60 (spherical), eluent: hexane/ethyl acetate=1/5), and dried at room temperature under reduced pressure to obtain 337 mg (yield 77%) of a title compound as a reddish brown solid.

Examples 42 to 45

By the same method as in Example 41, the reaction was carried out using equivalents of potassium tert-pentoxide (1.1 to 3.1 equivalents), at a reaction temperature (30° C. to 60° C.), for 0.5 to 1 hour, described in Table 6, and the reaction was evaluated using HPLC. The results are shown in Table 6.

TABLE 6

| | Potassium tert-pentoxide (equivalents) | Temperature (° C.) | Desired product:hydrolyzed product (HPLC %) | Yield (%) |
|---|---|---|---|---|
| Example 41 | 3.1 | 40 | 93.8:6.2 | 77 |
| Example 39 | 2.1 | 40 | 94.2:5.8 | — |
| Example 42 | 1.1 | 40 | 97.6:2.4 | 84 |
| Example 43 | 1.1 | 30 | 94.0:6.0 | — |
| Example 44 | 1.1 | 50 | 97.1:2.9 | — |
| Example 45 | 1.1 | 60 | 95.4:4.3 | — |

Under all the reaction conditions shown in Table 6, the side production of hydrolyzed products could be suppressed to less than 10% by the reaction of Step B (Example 39, 41 to 45). Particularly, the equivalents of potassium tert-pentoxide were investigated, and as a result, it was proved that if 2.1 equivalents were decreased to 1.1 equivalents at a reaction temperature of 40° C., the side production of hydrolyzed products could be controlled to less than 3% (Examples 39 and 42). Further, the reaction temperatures were investigated, and as a result, it was proved that a range from 40° C. to 50° C. was suitable (Examples 42 and 44).

In Tables 7 to 10, the reaction conversion rate and the diastereomer excess (de) are values calculated as follows, by carrying out HPLC measurement using the measurement condition E and taking the area percentages (%) of the obtained substrate, syn-forms, and anti-forms to give a total percentage of 100%.

$$\text{Reaction conversion rate}(\%)=\text{Syn-form}+\text{Anti form}/(\text{Substrate}+\text{Syn-form}+\text{Anti-form})\times 100$$

$$de(\%)=(\text{Anti-form}-\text{Syn-form})/(\text{Syn-form}+\text{Anti-form})\times 100$$

The substrate refer to benzyl 3-(cyclopropylcarbamoyl)-4-oxopyrrolidine-1-carboxylate, the syn-form refers to benzyl (3R,4R)-3-(cyclopropylcarbamoyl)-4-hydroxypyrrolidine-1-carboxylate, it's enantiomer, and a mixture thereof; and the anti-form refers to benzyl (3S,4R)-3-(cyclopropylcarbamoyl)-4-hydroxypyrrolidine-1-carboxylate, it's enantiomer, and a mixture thereof, respectively.

Measurement Condition E

Column; GL Sciences Inc., Inertsil ODS-3 (4.6ϕ×150 mm, 3 μm), pre-column; GL Sciences Inc., Inertsil ODS-3 (4.0ϕ×10 mm), mobile phase; Solution A: methanol, Solution B: diluted phosphoric acid (1→1000) solution containing 5 mmol of sodium 1-octanesulfonate, 0 to 30 minutes; A:B=42:58 (isocratic), detection wavelength: 215 nm, column temperature: 40° C., flow rate: 0.80 mL/min.

Retention time: substrate; approximately 22 minutes, syn-form; approximately 15 minutes, and anti-form; approximately 16 minutes.

In Tables 7 to 10, the enantiomer excess (ee) is a value calculated as follows, by carrying out HPLC measurement using the measurement condition F and taking the area percentages (%) of the obtained (3R,4S)-forms, (3S,4S)-forms, (3R,4R)-forms, and (3S,4R)-forms to give a total percentage of 100%.

$$ee(\%)=[(3S,4R)\text{-forms}-(3R,4S)\text{-forms}]/[(3S,4R)\text{-forms}+(3R,4S)\text{-forms}]\times 100$$

The (3R,4S)-form refers to benzyl (3R,4S)-3-(cyclopropylcarbamoyl)-4-hydroxypyrrolidine-1-carboxylate, the (3R,4R)-form refers to benzyl (3R,4R)-3-(cyclopropylcarbamoyl)-4-hydroxypyrrolidine-1-carboxylate, the (3S,4S)-form refers to benzyl (3S,4S)-3-(cyclopropylcarbamoyl)-4-hydroxypyrrolidine-1-carboxylate, and the (3S,4R)-form refers to benzyl (3S,4R)-3-(cyclopropylcarbamoyl)-4-hydroxypyrrolidine-1-carboxylate, respectively. In the case where the peaks of the (3R,4R)-form and the (3S,4R)-form were observed as a peak mixture, not separated completely from each other, the presence ratio, of each form was calculated from the above de, and used.

Measurement Condition F

Column; Daicel Chemical Industries, Ltd., Chiralpak AD-RH (4.6ϕ×150 mm) and Daicel Chemical Industries, Ltd., Chiralpak AD-3R (4.6ϕ×150 mm) connected, pre-column; GL Sciences Inc., Inertsil ODS-3 (4.0ϕ×10 mm), mobile phase; Solution A: acetonitrile, Solution B: diluted phosphoric acid (1→1000) solution, 0 to 30 minutes; A:B=25:75 (isocratic), detection wavelength: 215 nm, column temperature: 40° C., flow rate: 1.0 mL/min.

Retention time: (3R,4S)-form; approximately 12 minutes, (3S,4S)-form; approximately 16 minutes, (3R,4R)-form; approximately 20 minutes, and (3S,4R)-form; approximately 20 minutes.

Example 46

To benzyl 3-(cyclopropylcarbamoyl)-4-oxopyrrolidine-1-carboxylate were added a catalyst (dichlorobenzene ruthenium(II) dimer, 0.5 mol %), a chiral ligand [(S)-(−)-BINAP, 1.0 mol %], and a solvent (dichloromethane, 7.5-fold amount). The mixture was subjected to hydrogen substitution, and hydrogen pressure (0.5 to 0.6 MPa) was applied thereto, followed by stirring at an outer temperature of approximately 60° C. for 8 hours. The HPLC measurement of this reaction mixture was carried out. The results are shown in Table 7.

Examples 47 to 55 and Comparative Examples 1 to 2

By the same method as in Example 46, the reaction was carried out for 6 to 10 hours using the solvent (7.5-fold amount) described in Table 7. The results are shown in Table 7.

TABLE 7

| | Solvent | HPLC (%) Reaction conversion rate | de | ee |
|---|---|---|---|---|
| Example 46 | Dichloromethane | 100 | 97.1 | 94.9 |
| Example 47 | Methanol | 99.8 | 85.8 | 32.1 |
| Example 48 | 2-PrOH | 94.9 | 90.5 | 51.5 |
| Example 49 | $CF_3CH_2OH$ | 86.9 | 78.3 | 66.9 |
| Example 50 | DMF | 81.3 | 69.7 | 77.9 |
| Example 51 | Ethyl acetate | 100 | 92.6 | 83.5 |
| Example 52 | THF | 100 | 90.9 | 78.8 |
| Example 53 | Toluene | 97.2 | 97.0 | 89.3 |
| Example 54 | Chlorobenzene | 99.8 | 96.6 | 92.1 |
| Example 55 | Xylene | 90.3 | 96.3 | 88.4 |
| Comparative Example 1 | Acetonitrile | 0.5 | 3.0 | NT |
| Comparative Example 2 | Solkane ® 365mfc ($C_4H_5F_5$) | 0.1 | 52.4 | NT |

NT: Not tested (not measured)

In the case where dichloromethane was used as a solvent (Example 46), the reaction of Step A proceeded with good selectivity. In the case of using methanol (Example 47), 2-propanol (Example 48), 2,2,2-trifluoroethanol (Example 49), N,N-dimethylformamide (Example 50), ethyl acetate (Example 51), or tetrahydrofuran (Example 52), the selectivity was lowered, as compared with dichloromethane, but the reaction of Step A proceeded well.

Furthermore, in the case of using toluene (Example 53), chlorobenzene (Example 54), and xylene (Example 55), each of which is an aromatic solvent, the reaction of Step A proceeded with good selectivity. On other hand, in the case of using acetonitrile (Comparative Example 1) or Solkane (registered trademark) 365mfc (Comparative Example 2), the reaction of Step A substantially did not proceed.

Examples 56 to 62

By the same method as in Example 46, the reaction was carried out for 6 to 10 hours with the hydrogen pressure and the amount of the catalyst described in Table 8. The results are shown in Table 8.

TABLE 8

| | Pressure (MPa) | Amount of catalyst (mol %) | HPLC (%) Reaction conversion rate | de | ee |
|---|---|---|---|---|---|
| Example 56 | 2.5-2.7 | 2.0 | 100 | 95.3 | 87.2 |
| Example 57 | 0.8-0.9 | 2.0 | 100 | 96.0 | 91.2 |
| Example 58 | 0.5-0.6 | 2.0 | 100 | 96.3 | 91.2 |
| Example 59 | 0.3-0.4 | 2.0 | 100 | 96.3 | 92.0 |
| Example 60 | 0.1-0.2 | 2.0 | 100 | 96.5 | 93.7 |
| Example 61 | 0.5-0.6 | 0.5 | 100 | 95.3 | 87.9 |
| Example 62 | 0.5-0.6 | 0.1 | 100 | 95.1 | 84.0 |

In the case of changing the pressure in the range shown in Table 8 (Examples 56 to 60), the reaction of Step A proceeded with good selectivity in any case, and the pressure could be decreased to 0.1 to 0.2 MPa (Example 60). Further, also in the case of changing the amount of the catalyst (Examples 61 and 62), the reaction of Step A proceeded with good selectivity in any case, and the amount of the catalyst was decreased to 0.1 mol % (Example 62).

Examples 63 to 66

By the same method as in Example 46, the reaction was carried out for 6 to 10 hours using the chiral ligand described in Table 9. The results are shown in Table 9.

TABLE 9

| | Chiral ligand | HPLC (%) Reaction conversion rate | de | ee |
|---|---|---|---|---|
| Example 46 | (S)-BINAP | 100 | 97.1 | 94.9 |
| Example 63 | (S)-TolBINAP | 100 | 96.0 | 94.4 |
| Example 64 | (S)-SEGPHOS | 100 | 95.3 | 98.7 |
| Example 65 | (S)-DM-SEGPHOS | 100 | 96.5 | 98.3 |
| Example 66 | (S)-MeO-BIPHEP | 100 | 95.1 | 96.9 |

In the case of using the chiral ligand shown in Table 9 (Examples 63 to 66), the reaction of Step A also proceeded while maintaining good selectivity. Particularly, in the case of using (S)-SEGPHOS (Example 64), (S)-DM-SEGPHOS (Example 65), or (S)-MeO-BIPHEP (Example 66), it was confirmed that the optical purity (ee) was enhanced in any case, as compared with a case of (S)-BINAP.

Example 67

To benzyl 3-(cyclopropylcarbamoyl)-4-oxopyrrolidine-1-carboxylate were added a catalyst (dichlorobenzene ruthenium(II) dimer, 0.5 mol %), a chiral ligand [(S)-(−)-BINAP, 1.0 mol %], and a solvent (toluene, 7.5-fold amount). The mixture was replaced by hydrogen, and hydrogen pressure (0.5 to 0.6 MPa) was applied thereto, followed by stirring at an outer temperature of approximately 55° C. for 8 hours. The HPLC measurement of this reaction mixture was carried out. The results are shown in Table 10.

Examples 68 to 70

By the same method as in Example 67, the reaction was carried out for 6 to 10 hours at the temperature described in Table 10. The results are shown in Table 10.

TABLE 10

| | Temperature (° C.) | HPLC (%) Reaction conversion rate | de | ee |
|---|---|---|---|---|
| Example 53 | 60 | 97.2 | 97.0 | 89.3 |
| Example 67 | 55 | 65.7 | 96.7 | 89.5 |
| Example 68 | 70 | 97.3 | 96.3 | 87.8 |
| Example 69 | 80 | 100 | 96.0 | 88.3 |
| Example 70 | 100 | 100 | 92.1 | 83.1 |

In the case of changing the temperatures in the range shown in Table 10 using toluene as a solvent (Examples 67 to 70), the reaction of Step A proceeded with good selectivity in any case. In the case of changing the temperature, a decrease in the reaction conversion rate was observed with a decrease in the temperature, as compared with a case with 60° C. (Example 67), whereas a slight decrease in the selectivity was observed with an increase in the temperature (Examples 68 to 70).

Reference Example 2 tert-Butyl 3-{N-benzyloxycarbonyl-N-(ethoxycarbonylmethyl)amino}propionate

[Chem. 19]

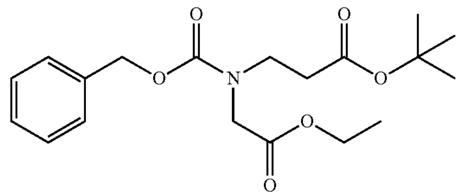

To glycine ethyl ester hydrochloride (817 g, 5.85 mol) were added water (750 mL) and 2-propanol (2.3 L), followed by warming the mixture and triethylamine (870 mL, 6.24 mol) was added thereto at an internal temperature of from 55° C. to 57° C. To the mixed liquid was added dropwise tert-butyl acrylate (250 g, 1.95 mol) at an internal temperature of from 60° C. to 62° C., followed by stirring at an internal temperature of from 60° C. to 62° C. for 2 hours.

Furthermore, tert-butyl acrylate (250 g, 1.95 mol) was added dropwise to the mixed liquid at an internal temperature of from 63° C. to 64° C., followed by stirring at an internal temperature of from 63° C. to 64° C. for 1 hour. The mixed liquid was cooled to an internal temperature of 30° C. and allowed to stand overnight. The mixed liquid was warmed again and stirred at an internal temperature of from 55° C. to 64° C. for 2 hours. The mixed liquid was cooled to an internal temperature of 30° C., and then 3% sodium hydrogen carbonate (5 L) was added thereto, followed by extraction with ethyl acetate (5 L). The organic layer was collected by separation.

To the ethyl acetate solution was added a sodium hydrogen carbonate solution (328 g (3.90 mol) of sodium hydrogen carbonate had been dissolved in 6.5 L of water) at an internal temperature of from 25° C. to 30° C., and benzyl chloroformate (557 mL, 3.90 mol) was added dropwise thereto at an internal temperature of from 29° C. to 36° C., followed by stirring at an internal temperature of from 30° C. to 33° C. for 2 hours. The reaction mixture was cooled to an internal temperature of 24° C. and the organic layer was collected by separation. The organic layer was sequentially washed with 0.5 mol/L hydrochloric acid (2.5 L) and 5% brine (2.5 L), and concentrated under reduced pressure to obtain 1329 g of a title compound as a reddish brown oil.

$^1$H NMR (400 MHz, $CDC1_3$) δ: 1.19 (1.5H, t, J=7.3 Hz), 1.26 (1.5H, t, J=7.3 Hz), 1.43 (9H, s), 2.53 (1H, t, J=6.4 Hz), 2.59 (1H, t, J=6.4 Hz), 3.56-3.61 (2H, m), 4.05-4.21 (4H, m), 5.11 (1H, s,) 5.17 (1H,s), 7.30-7.38 (5H, m).

Example 71

3-{N-Benzyloxycarbonyl-N-(ethoxycarbonylmethyl) amino}propionic acid

[Chem. 20]

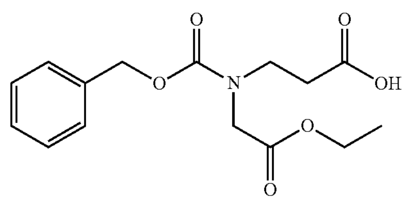

To tert-butyl 3-{N-benzyloxycarbonyl-N-(ethoxycarbonylmethyl)amino}propionate (corresponding to 1329 g, 3.90 mol) synthesized by the method of Reference Example 2 was added formic acid (4 L, 106 mol) at an internal temperature of from 35° C. to 40° C., followed by stirring at an internal temperature of from 40° C. to 50° C. for 3.5 hours.

The reaction mixture was cooled and 5% brine (10 L) was put thereinto. Then, a toluene/DME (4:1) mixed liquid (10 L) was added thereto, followed by extraction. To the organic layer was added 20% potassium hydrogen carbonate (5 L) and the aqueous layer was collected by separation. To the aqueous layer was added 6 mol/L hydrochloric acid (2 L) at an internal temperature of from 10° C. to 11° C. to adjust to approximately pH 1, followed by extracting with a toluene/DME (4:1) mixed liquid (7 L). The organic layer was collected by separation, washed with water (3.5 L), and concentrated under reduced pressure. To the concentrated residue was added toluene (1.5 L), followed by concentrating under reduced pressure, to obtain 796 g of a title compound as a brown oily substance.

$^1$H NMR (400 MHz, $CDC1_3$) δ: 1.18 (1.5H, t, J=7.0 Hz), 1.26 (1.5H, t, J=7.0 Hz) 2.67 (1H, t, J=6.76 Hz), 2.75 (1H, t, J=6.4 Hz), 3.60-3.64 (2H, m), 4.05-4.21 (4H, m), 5.12 (1H,s), 5.17 (1H,s), 7.28-7.36 (5H, m).

Example 72

Ethyl N-benzyloxycarbonyl-N-{(2-cyclopropylaminocarbonyl)ethyl}aminoacetate

[Chem. 21]

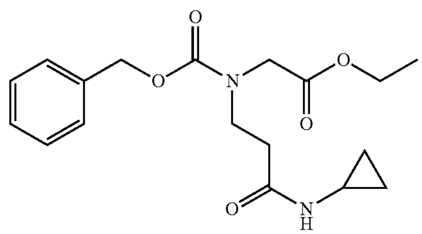

To 3-{N-benzyloxycarbonyl-N-(ethoxycarbonylmethyl) amino}propionic acid (corresponding to 796 g, 2.57 mol) synthesized by the method of Example 71 was added THF (4.3 L). HOBt.$H_2O$ (21.5 g, 0.140 mol), triethylamine (435 mL, 3.12 mol), cyclopropylamine (216 mL, 3.12 mol), and EDCI.HCl (627 g, 4.10 mol) were sequentially added to the mixed liquid, followed by stirring at an internal temperature of from 35° C. to 49° C. for 2 hours.

The reaction mixture was cooled to an internal temperature of 17° C., water (8 L) and toluene (8 L) were added thereto, followed by stirring and extracting, and the organic layer was collected by separation. The organic layer was sequentially washed with 1 mol/L hydrochloric acid (4 L) and water (2 L), and concentrated under reduced pressure. To the concentrated residue was added toluene (1.5 L), followed by concentrating under reduced pressure. To the concentrated residue were added acetone (0.5 L) and diisopropylether (14.5 L), followed by warming, crystallizing at an internal temperature of 35° C., and then stirring at an internal temperature of from 30° C. to 33° C. for 0.5 hours.

The mixed liquid was slowly cooled and then stirring at an internal temperature of from 5° C. to 9° C. for 0.5 hours. The precipitated crystal was collected by filtration and washed with diisopropyl ether (2.5 L). The wet crystal was dried at 40° C. overnight under reduced pressure to obtain 689 g (yield 51%, 4 steps) of a title compound as a slightly yellowish white crystal.

$^1$H NMR (400 MHz, $CDCl_3$) δ: 0.42-0.48 (2H, m), 0.69-0.75 (2H, m), 1.23 (3H, dt, J=26.2, 7.0 Hz), 2.34-2.68 (3H, m), 3.62-3.68 (2H, m), 4.03-4.23 (4H, m), 5.10-5.19 (2H, m), 6.20 (1H, br s), 7.26-7.38 (5H, m).

Example 73

Benzyl 3-(cyclopropylcarbamoyl)-4-oxopyrrolidine-1-carboxylate

[Chem. 22]

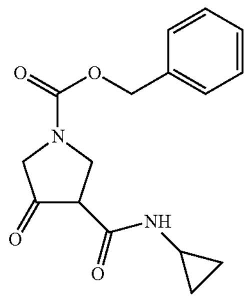

To ethyl N-benzyloxycarbonyl-N-{(2-cyclopropylaminocarbonyl)ethyl}aminoacetate (600 g, 1.72 mol) synthesized by the method of Example 72 was added toluene (6 L), and then to the mixed liquid was added dropwise a 1.7 mol/L solution (1.11 L, 1.89 mol) of potassium tert-pentoxide in toluene at an internal temperature of from 46° C. to 48° C., followed by stirring at an internal temperature of from 48° C. to 49° C. for 2 hours. The reaction mixture was cooled and then adjusted to pH 1.2 (pH-meter) by the addition dropwise of 1 mol/L hydrochloric acid (2.1 L) at an internal temperature of from 4° C. to 7° C.

The mixture was extracted with ethyl acetate (6 L), washed with water (3 L), and then concentrated under reduced pressure. To the concentrated residue was added 2-propanol (2.1 L), followed by heating and dissolving, and then water (3.9 L) was added dropwise thereto at an internal temperature of from 64° C. to 68° C., followed by cooling to an internal temperature of 55° C. After cooling to an internal temperature of 35° C. and crystallizing, the mixed liquid was warmed to an internal temperature of 45° C.

Water (2.4 L) was further added thereto at an internal temperature of from 45° C. to 46° C., followed by stirring at an internal temperature of from 45° C. to 46° C. for 0.5 hours. The mixture was cooled to an internal temperature of 25° C. and stirred at an internal temperature of from 20° C. to 25° C. for 0.5 hours. The precipitated crystal was collected by filtration and washed with a 2-propanol/water (1:3) mixed liquid (3 L). The wet crystal was dried at 50° C. for overnight under reduced pressure to obtain 448 g (yield 86%) of a title compound as a pale brown crystal.

$^1$H NMR (400 MHz, $CDCl_3$) δ: 0.50-0.58 (2H, m), 0.75-0.85 (2H, m), 2.69-2.77 (1H, m), 3.41 (1H, t, J=8.8 Hz), 3.86-4.07 (2H, m), 4.20-4.27 (2H, m), 5.15-5.23 (2H, m), 6.60-6.80 (1H, m), 7.30-7.44 (5H, m).

Example 74

Benzyl (3S,4R)-3-(cyclopropylcarbamoyl)-4-hydroxypyrrolidine-1-carboxylate

[Chem. 23]

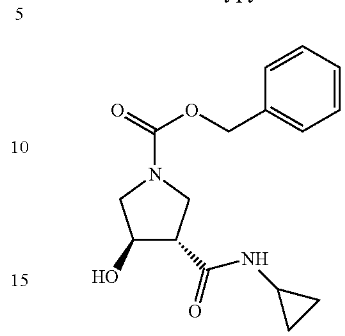

To benzyl 3-(cyclopropylcarbamoyl)-4-oxopyrrolidine-1-carboxylate (26.0 g, 86.0 mmol) synthesized by the method of Example 73 were added a dichlorobenzene ruthenium(II) dimer (21.5 mg, 43.0 μmol), (S)-2,2'-bis(diphenylphosphino)-1,1-binaphthyl[(S)-(−)-BINAP] (53.6 mg, 86.0 μmol), and dichloromethane (196 mL). The mixture was replaced by hydrogen and the initial hydrogen pressure was adjusted to 1.0 MPa, and the mixture was stirred at an outer temperature of approximately 60° C. for 10 hours.

Hydrogen was released and then the reaction mixture was concentrated under reduced pressure. To the residue was added ethyl acetate (364 mL), followed by heating to an internal temperature of approximately 74° C. and dissolving, and then cooling to an internal temperature of 18° C. The precipitated solid was collected by filtration and washed with ethyl acetate (119 mL). After drying at 50° C. for 2 hours under reduced pressure, 21.3 g (yield 81%) of a title compound as a white floss crystal was obtained.

Melting point (hot plate method): 134.4° C. to 135.0° C.

$^1$H NMR ($CDCl_3$, 400 MHz) δ: 0.45-0.77 (2H, m), 0.69-0.77 (2H, m), 2.63-2.82 (2H, m), 3.19-3.29 (1H, m), 3.49-3.85 (3H, m), 3.91-4.15 (1H, m), 4.35-4.49 (1H, m), 5.10 (2H, s), 6.57 (1H, d, J=15.9 Hz), 7.26-7.37 (5H, m).

Chemical purity: 98.3% (99.6% de, retention time: 17.0 minutes), column; GL Sciences Inc., Inertsil ODS-3 (4.6ϕ×150 mm, 3 μm), pre-column; GL Sciences Inc., Inertsil ODS-3 (4.0ϕ×10 mm), mobile phase; Solution A: methanol, Solution B: diluted phosphoric acid (1→1000) solution containing 5 mmol of sodium 1-octanesulfonate, 0 to 30 minutes; A:B=42:58 (isocratic), detection wavelength: 215 nm, column temperature: 40° C., flow rate: 0.80 mL/min.

Optical purity: 100% ee (retention time: 16.4 minutes), column; Daicel Chemical Industries, Ltd., Chiralpak AD-RH (4.6ϕ×150 mm)+Daicel Chemical Industries, Ltd., Chiralpak AD-3R (4.6ϕ×150 mm), pre-column; GL Sciences Inc., Inertsil ODS-3 (4.0ϕ×10 mm), mobile phase; Solution A: acetonitrile, Solution B: diluted phosphoric acid (1→1000) solution, 0 to 30 minutes; A:B=25:75 (isocratic), detection wavelength: 215 nm, column temperature: 40° C., flow rate: 1.0 mL/min In Tables 11 to 12, the reaction conversion rates were values calculated as follows, by carrying out HPLC measurement using the measurement condition G below and taking the area percentages (%) of the obtained substrate, syn-form, and anti-form to give a total percentage of 100%.

Reaction conversion rate(%)=Syn-form+Anti-form/(Substrate+Syn-form+Anti-form)×100

The substrate refers to a 1-benzyl 3-ethyl 4-oxopyrrolidine-1,3-dicarboxylate and the desired product refers to a 1-benzyl 3-ethyl anti-(3R,4S)-4-hydroxypyrrolidine-1,3-dicarboxylate, respectively.

Measurement Condition G

Column; GL Sciences Inc., Inertsil ODS-3 (4.6ϕ×150 mm), pre-column; GL Sciences Inc., Inertsil ODS-3 (4.0ϕ×10 mm), mobile phase; Solution A: diluted phosphoric acid (1→1000) solution, Solution B: acetonitrile, 0 to 30 minutes; A:B=50:50 (isocratic), detection wavelength: 210 nm, column temperature: 30° C., flow rate: 1.0 mL/min., retention time: desired product; approximately 4 minutes, raw material; approximately 7 minutes In Tables 11 to 12, de was a value calculated as follows, by carrying out HPLC measurement using the measurement condition H below and taking the area percentages (%) of the obtained substrate, syn-form, and anti-form to give a total percentage of 100%.

$$de\ (\%) = (\text{Anti-form} - \text{Syn-form})/(\text{Syn-form} + \text{Anti-form}) \times 100$$

In Tables 11 to 12; ee was a value calculated as follows, by carrying out HPLC measurement using the measurement condition H below and taking the area percentages (%) of the obtained (3R,4S)-forms, (3S,4S)-forms, (3R,4R)-forms, and (3S,4R)-forms to give a total percentage of 100%.

$$ee\ (\%) = [(3R,4S)\text{-form} - (3S,4R)\text{-form}]/[(3R,4S)\text{-form} + (3S,4R)\text{-form}] \times 100$$

The (3R,4S)-form refers to 1-benzyl 3-ethyl (3R,4S)-4-hydroxypyrrolidine-1,3-dicarboxylate, the (3R,4R)-form refers to 1-benzyl 3-ethyl (3R,4R)-4-hydroxypyrrolidine-1,3-dicarboxylate, the (3S,4S)-form refers to 1-benzyl 3-ethyl (3S,4S)-4-hydroxypyrrolidine-1,3-dicarboxylate, and the (3R,4S)-form refers to 1-benzyl 3-ethyl (3R,4S)-4-hydroxypyrrolidine-1,3-dicarboxylate, respectively.

Measurement Condition H

Column; Daicel Chemical Industries, Ltd., Chiralcel AD-RH (4.6ϕ×150 mm), pre-column; GL Sciences Inc., Inertsil ODS-3 (4.0ϕ×10 mm), mobile phase; Solution A: diluted phosphoric acid (1→1000) solution, Solution B: acetonitrile, 0 to 30 minutes; A:B=80:20 (isocratic), detection wavelength: 210 nm, column temperature: 50° C., flow rate: 1.0 mL/min., retention time: desired product; approximately 23 minutes, enantiomer; approximately 18 minutes, diastereomer; approximately 23 minutes and 28 minutes.

Reference Examples 3 to 7

A dichlorobenzene ruthenium(II) dimer (172 mg, 0.34 mmol), (S)-(−)-BINAP (428 mg, 0.69 mmol), and dichloromethane (3.7 mL) were added, followed by stirring at an outer temperature of from 60° C. to 65° C. for 0.5 hours and then cooling to a temperature of approximately room temperature.

To a mixture were added a 1-benzyl 3-ethyl 4-oxopyrrolidine-1,3-dicarboxylate (5.0 g, 17.2 mmol) and dichloromethane (15 mL) under an argon atmosphere, followed by stirring at an internal temperature of from 60° C. to 65° C. for 8 hours under hydrogen pressurization. The HPLC measurement of this reaction mixture was carried out. The results are shown in Table 11.

TABLE 11

| | | HPLC (%) | | |
|---|---|---|---|---|
| | Hydrogen pressure (MPa) | Reaction conversion rate | de | ee |
| Reference Example 3 | 0.5-0.6 | 42 | — | — |
| Reference Example 4 | 1.0-1.3 | 100 | 84 | 86 |
| Reference Example 5 | 2.0-2.5 | 100 | 84 | 85 |
| Reference Example 6 | 5 | 100 | 84 | 84 |
| Reference Example 7 | 10 | 100 | 85 | 83 |

Reference Examples 3 to 7 are prior arts described in International Publication WO 2007/102567, and are each an asymmetric hydrogenation reaction of 1-benzyl 3-ethyl 4-oxopyrrolidine-1,3-dicarboxylate. It can be seen that if the hydrogen pressure is lowered to from 0.5 to 0.6 MPa, the reaction conversion rate is lowered (Reference Example 3).

On the other hand, according to the present invention, as shown in Examples 46 to 55 and 58 to 70, the reaction proceeds without a decrease in the reaction conversion rate even at a low pressure of from 0.5 to 0.6 MPa or lower. The reaction under the high pressure condition is not industrially suitable and has a high risk of explosion, and therefore, it can be said that the present invention is more useful than prior arts.

Reference Examples 8 to 10

A dichlorobenzene ruthenium(II) dimer, (S)-(−)-BINAP, and dichloromethane (3.7 mL) were added, followed by stirring at an outer temperature of from 60° C. to 65° C. for 0.5 hours and then cooling to a temperature of approximately room temperature. To the mixture were added a 1-benzyl 3-ethyl 4-oxopyrrolidine-1,3-dicarboxylate (5.0 g, 17.2 mmol) and dichloromethane (15 mL) under an argon atmosphere, followed by stirring at an internal temperature of from 60° C. to 65° C. for 8 hours under hydrogen pressurization of from 2.0 to 2.5 MPa. The HPLC measurement of this reaction mixture was carried out. The results are shown in Table 12.

TABLE 12

| | Amount of catalyst (mol %) | HPLC (%) Reaction conversion rate |
|---|---|---|
| Reference Example 8 | 4 | 100 |
| Reference Example 9 | 2 | 100 |
| Reference Example 10 | 1 | 70 |

Reference Example 8 to Reference Example 10 are prior arts described in International Publication WO 2007/102567, and are an asymmetric hydrogenation reaction of 1-benzyl 3-ethyl 4-oxopyrrolidine-1,3-dicarboxylate. It can be seen that if the amount of the catalyst is decreased to 1 mol %, the reaction conversion rate is decreased (Reference Example 10).

On the other hand, according to the present invention, as shown in Examples 46 to 55, 61 to 66, 68 to 70 and 74, the reaction proceeded without a decrease in the reaction conversion rate even at the amount of the catalyst of 1 mol % or less, or even lower amounts. From the viewpoint that optically active catalysts are expensive, it can be said that the present invention in which the reaction proceeds with a small amount of the catalyst is industrially excellent.

The present invention is described in detail and with reference to specific embodiments, but it is apparent to persons skilled in the art that various changes or modifications may be added without departing from the spirit or scope of the present invention.

The present application is based on Japanese Patent Application No. 2010-238077, filed on Oct. 25, 2010, the content of which is hereby incorporated by reference.

INDUSTRIAL APPLICABILITY

The present invention allows industrially advantageous preparation of an optically active form of an anti-(3S,4R)-3-alkylcarbamoyl-4-hydroxypyrrolidine derivative or it's enantiomer, which is a key intermediate for producing a high-quality optically active form of (3R,4S)-3-alkylaminomethyl-4-fluoropyrrolidine or it's enantiomer useful as an intermediate for producing a pharmaceutical, and is thus useful.

The invention claimed is:

1. A method for producing an optically active anti-4-hydroxypyrrolidine-3-carboxamide compound represented by formula (II) or its enantiomer, (II)

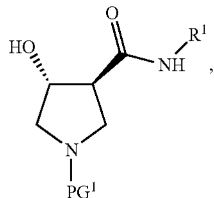

wherein $PG^1$ represents a protecting group for an amino group and $R^1$ represents hydrogen, a C1 to C6 alkyl group which may be substituted, or a C3 to C8 cycloalkyl group which may be substituted, the method comprising:

subjecting a 4-oxopyrrolidine-3-carboxamide compound represented by formula (I) to an asymmetric hydrogenation using an optically active catalyst having a chiral ligand under a hydrogen pressure of from 0.1 MPa to less than 1 MPa, wherein the chiral ligand is selected from the group consisting of (i) an optionally active 2,2'-bis(diphenylphosphino)-1,1'-binaphthyl (BINAP), (ii) 5,5'-bis(diphenylphosphino)-4,4'-bi-1,3-benzodioxle (SEGPHOS), (iii) (2,2'-bisdiphenylphosphino)-6,6'-dimethoxy-1,1'-biphenyl (MeO-BIPHEP), and (iv) (S)-(−)-2,2'-bis(di-p-tolylphosphino)-1,1'-binaphthyl ((S)-TolBINAP) (Step A), (I)

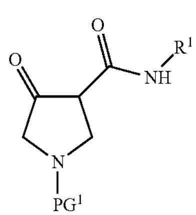

wherein $PG^1$ and $R^1$ are as defined above.

2. A method for producing an optically active anti-4-hydroxypyrrolidine-3-carboxamide compound represented by formula (II) or its enantiomer, (II)

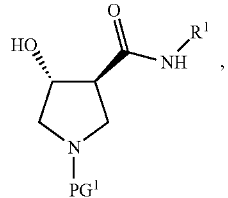

wherein $PG^1$ represents a protecting group for an amino group and $R^1$ represents hydrogen, a C1 to C6 alkyl group which may be substituted, or a C3 to C8 cycloalkyl group which may be substituted, the method comprising Steps B and A below:

(Step B) a step of treating a compound represented by formula (III), (III)

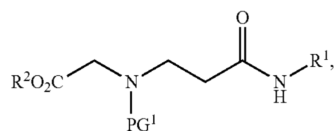

wherein $PG^1$ and $R^1$ are as defined above, and $R^2$ represents a C1 to C6 alkyl group, with at least one base selected from the group consisting of an alkali metal carbonate, an alkali metal amide, an alkali metal hydride, and an alkali metal alkoxide, to obtain a 4-oxopyrrolidine-3-carboxamide compound represented by formula (I), (I)

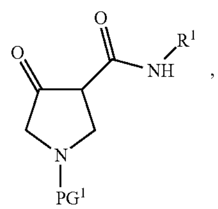

wherein $PG^1$ and $R^1$ are as defined above; and (Step A) a step of subjecting the compound represented by the formula (I) obtained in Step B to an asymmetric hydrogenation using an optically active catalyst having a chiral ligand under a hydrogen pressure of from 0.1 MPa to less than 1 MPa, wherein the chiral ligand is selected from the group consisting of (i) an optionally active 2,2'-bis(diphenylphosphino)-1,1'-binaphthyl (BINAP), (ii) 5,5'-bis(diphenylphosphino)-4,4'-bi-1,3-benzodioxle (SEGPHOS), (iii) (2,2'-bisdiphenylphosphino)-6,6'-dimethoxy-1,1'-biphenyl (MeO-BIPHEP), and (iv) (S)-(−) -2,2'-bis(di-p-tolylphosphino)-1,1'-binaphthyl ((S)-TolBINAP), to obtain the compound represented by the formula (II) or its enantiomer.

3. A method for producing an optically active anti-4-hydroxypyrrolidine-3-carboxamide compound represented by formula (II) or its enantiomer, (II)

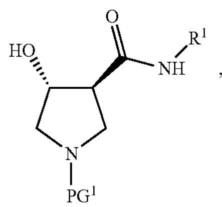

wherein $PG^1$ represents a protecting group for an amino group and $R^1$ represents hydrogen, a C1 to C6 alkyl group which may be substituted, or a C3 to C8 cycloalkyl group which may be substituted, the method comprising Steps D to A below:

(Step D) a step of treating a compound represented by formula (IV), (IV)

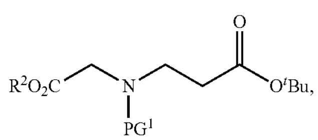

wherein $PG^1$ is as defined above and $R^2$ represents a C1 to C6 alkyl group, with an acid, to obtain a compound represented by formula (V), (V)

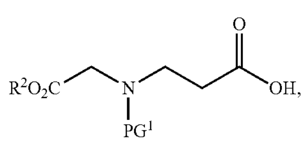

wherein $PG^1$ and $R^2$ are as defined above;

(Step C) a step of condensing the compound represented by the formula (V) obtained in Step D with an amine represented by formula (VI), $$R^1\text{—}NH_2 \quad \text{(VI)}$$

wherein $R^1$ is as defined above, to obtain a compound represented by formula (III), (III)

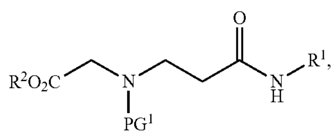

wherein $PG^1$, $R^1$ and $R^2$ are each as defined above;

(Step B) a step of treating the compound represented by the formula (III) obtained in Step C with at least one base selected from the group consisting of an alkali metal carbonate, an alkali metal amide, an alkali metal hydride, and an alkali metal alkoxide, to obtain a 4-oxopyrrolidine-3-carboxamide compound represented by formula (I), (I)

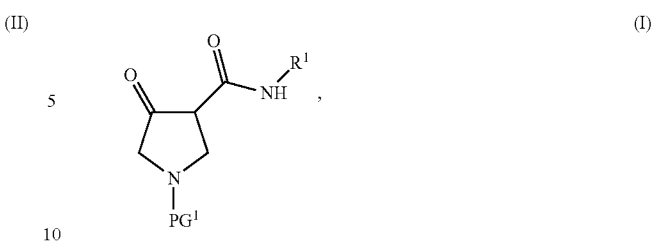

wherein $PG^1$ and $R^1$ are each as defined above;

(Step A) a step of subjecting the compound represented by the formula (I) obtained in Step B to an asymmetric hydrogenation using an optically active catalyst having a chiral ligand under a hydrogen pressure of from 0.1 MPa to less than 1 MPa, wherein the chiral ligand is selected from the group consisting of (i) an optionally active 2,2'-bis(diphenylphosphino)-1,1'-binaphthyl (BINAP), (ii) 5,5'-bis(diphenylphosphino)-4,4'-bi-1,3-benzodioxle (SEGPHOS), (iii) (2,2'-bisdiphenylphosphino)-6,6'-dimethoxy-1,1'-biphenyl (MeO-BIPHEP), and (iv) (S)-(−)-2,2'-bis(di-p-tolylphosphino)-1,1'-binaphthyl ((S)-TolBINAP), to obtain the compound represented by the formula (II) or its enantiomer.

4. The method according to claim 1, wherein the optically active catalyst in Step A is an optically active ruthenium catalyst having a chiral ligand.

5. The method according to claim 1, wherein in Step A, the chiral ligand in the optically active catalyst is 2,2'-bis(diphenylphosphino)-1,1'-binaphthyl (BINAP) or 5,5'-bis(diphenylphosphino)-4,4'-bi-1,3-benzodioxole (SEGPHOS).

6. The method according to claim 1, wherein the protecting group for the amino group represented by $PG^1$ is an aralkoxycarbonyl group or an alkoxycarbonyl group.

7. The method according to claim 1, wherein the protecting group for the amino group represented by $PG^1$ is an aralkoxycarbonyl group.

8. The method according to claim 1, wherein the protecting group for the amino group represented by $PG^1$ is a benzyloxycarbonyl group.

9. The method according to claim 1, wherein $R^1$ is a cyclopropyl group.

10. The method according to claim 1, wherein the optically active catalyst in Step A is used in an amount of from 0.01 to 2 mol %, with respect to the compound of formula (I).

11. The method according to claim 1, wherein the optically active catalyst in Step A is used in an amount of from 0.01 to 1 mol %, with respect to the compound of formula (I).

12. The method according to claim 2, wherein the base in Step B is an alkali metal alkoxide.

13. The method according to claim 2, wherein the base in Step B is potassium tert-pentoxide.

14. The method according to claim 2, wherein the base in Step B is used in the amount of from 1 to 1.5 equivalents, with respect to the compound represented by the formula (III).

15. The method according to claim 1, wherein the protecting group for the amino group represented by $PG^1$ is an aralkoxycarbonyl group and $R^1$ is a cyclopropyl group.

16. The method according to claim 3, wherein the acid in Step D is trifluoroacetic acid or formic acid.

17. The method according to claim 3, wherein the acid in Step D is formic acid.

18. The method according to claim 2, wherein the protecting group for the amino group represented by $PG^1$ is an aralkoxycarbonyl group and $R^2$ is a C1 to C4 lower alkyl group.

* * * * *